United States Patent
Iida et al.

(10) Patent No.: US 8,868,372 B2
(45) Date of Patent: Oct. 21, 2014

(54) POSITION DETECTING SYSTEM AND POSITION DETECTING METHOD

(75) Inventors: Takahiro Iida, Hachioji (JP); Atsushi Chiba, Hachioji (JP); Atsushi Kimura, Akiruno (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 12/879,441

(22) Filed: Sep. 10, 2010

(65) Prior Publication Data
US 2011/0184690 A1    Jul. 28, 2011

Related U.S. Application Data

(63) Continuation of application No. PCT/JP2010/050406, filed on Jan. 15, 2010.

(30) Foreign Application Priority Data

Mar. 10, 2009  (JP) .................... 2009-057018

(51) Int. Cl.
| | |
|---|---|
| *G01C 9/00* | (2006.01) |
| *G01C 19/00* | (2013.01) |
| *A61B 1/04* | (2006.01) |
| *G06F 3/01* | (2006.01) |
| *A61B 19/00* | (2006.01) |
| *A61B 5/06* | (2006.01) |
| *A61B 1/00* | (2006.01) |
| *A61B 1/06* | (2006.01) |
| *A61B 5/00* | (2006.01) |

(52) U.S. Cl.
CPC ............. *A61B 1/041* (2013.01); *G06F 3/011* (2013.01); *A61B 19/5244* (2013.01); *A61B 1/00016* (2013.01); *A61B 1/00032* (2013.01); *A61B 1/00158* (2013.01); *A61B 1/0684* (2013.01); *A61B 5/7257* (2013.01); *A61B 5/062* (2013.01)

USPC .......................................................... 702/150

(58) Field of Classification Search
CPC ........ G06F 3/011; G01C 15/00; A61B 5/065; A61B 19/5244; A61B 2019/5251; A61B 2019/5272
USPC .......................................................... 702/150
See application file for complete search history.

(56) References Cited

U.S. PATENT DOCUMENTS

| 8,049,503 B2 * | 11/2011 | Kimura et al. ........... 324/319 |
| 2005/0216231 A1 | 9/2005 | Aoki et al. |

(Continued)

FOREIGN PATENT DOCUMENTS

| CN | 1968648 | 5/2007 |
| CN | 101010026 A | 8/2007 |

(Continued)

OTHER PUBLICATIONS

International Search Report dated Feb. 16, 2010.

(Continued)

*Primary Examiner* — Michael Nghiem
(74) *Attorney, Agent, or Firm* — Scully, Scott, Murphy & Presser, P.C.

(57) ABSTRACT

A position detecting system having a predicting unit for calculating a moving amount by which a detected object is predicted to move between a first time and a second time after a predetermined time from the first time, and for predicting at least one of a position and a direction of the detected object at the second time, and a control unit for controlling a position detecting unit based on the at least one of the position and the direction of the detected object at the second time predicted by the predicting unit.

18 Claims, 8 Drawing Sheets

(56) References Cited

U.S. PATENT DOCUMENTS

| | | | |
|---|---|---|---|
| 2006/0252987 A1 | 11/2006 | Hasegawa et al. | |
| 2007/0197869 A1* | 8/2007 | Uchiyama et al. | 600/114 |
| 2007/0238987 A1 | 10/2007 | Minai et al. | |
| 2007/0244388 A1 | 10/2007 | Sato et al. | |
| 2008/0039688 A1* | 2/2008 | Minal et al. | 600/117 |
| 2008/0139883 A1* | 6/2008 | Uchiyama | 600/117 |
| 2008/0177177 A1 | 7/2008 | Aoki et al. | |
| 2008/0177178 A1 | 7/2008 | Aoki et al. | |
| 2008/0281188 A1 | 11/2008 | Aoki et al. | |
| 2008/0300459 A1* | 12/2008 | Kimura et al. | 600/118 |
| 2008/0306340 A1* | 12/2008 | Uchiyama et al. | 600/117 |
| 2008/0312501 A1* | 12/2008 | Hasegawa et al. | 600/117 |
| 2009/0171190 A1* | 7/2009 | Uchiyama et al. | 600/424 |
| 2009/0237073 A1* | 9/2009 | Uchiyama et al. | 324/207.11 |
| 2009/0299142 A1* | 12/2009 | Uchiyama et al. | 600/118 |
| 2010/0010306 A1* | 1/2010 | Kawano et al. | 600/118 |
| 2010/0073185 A1 | 3/2010 | Uchiyama et al. | |
| 2010/0204566 A1* | 8/2010 | Uchiyama et al. | 600/424 |
| 2010/0219825 A1 | 9/2010 | Sato et al. | |
| 2010/0305426 A1* | 12/2010 | Kimura et al. | 600/411 |
| 2011/0012594 A1* | 1/2011 | Kimura et al. | 324/309 |
| 2011/0184690 A1* | 7/2011 | Iida et al. | 702/150 |

FOREIGN PATENT DOCUMENTS

| | | |
|---|---|---|
| EP | 1 704 812 A1 | 9/2006 |
| EP | 2 016 897 A1 | 1/2009 |
| JP | 2005-136828 | 5/2005 |
| JP | 2005-198789 | 7/2005 |
| JP | 2005-245963 | 9/2005 |
| JP | 2006-026391 | 2/2006 |
| JP | 2006-192252 | 7/2006 |
| JP | 2006-271520 | 10/2006 |
| JP | 2007-175317 | 7/2007 |
| JP | 2008-132047 | 6/2008 |
| WO | WO 2007/074767 A1 | 7/2007 |
| WO | WO 2010/103866 * | 9/2010 |

OTHER PUBLICATIONS

Japanese Office Action dated Nov. 2, 2010.

Extended Supplementary Partial European Search Report dated Feb. 13, 2013 in European Patent Application No. 10750622.2.

* cited by examiner

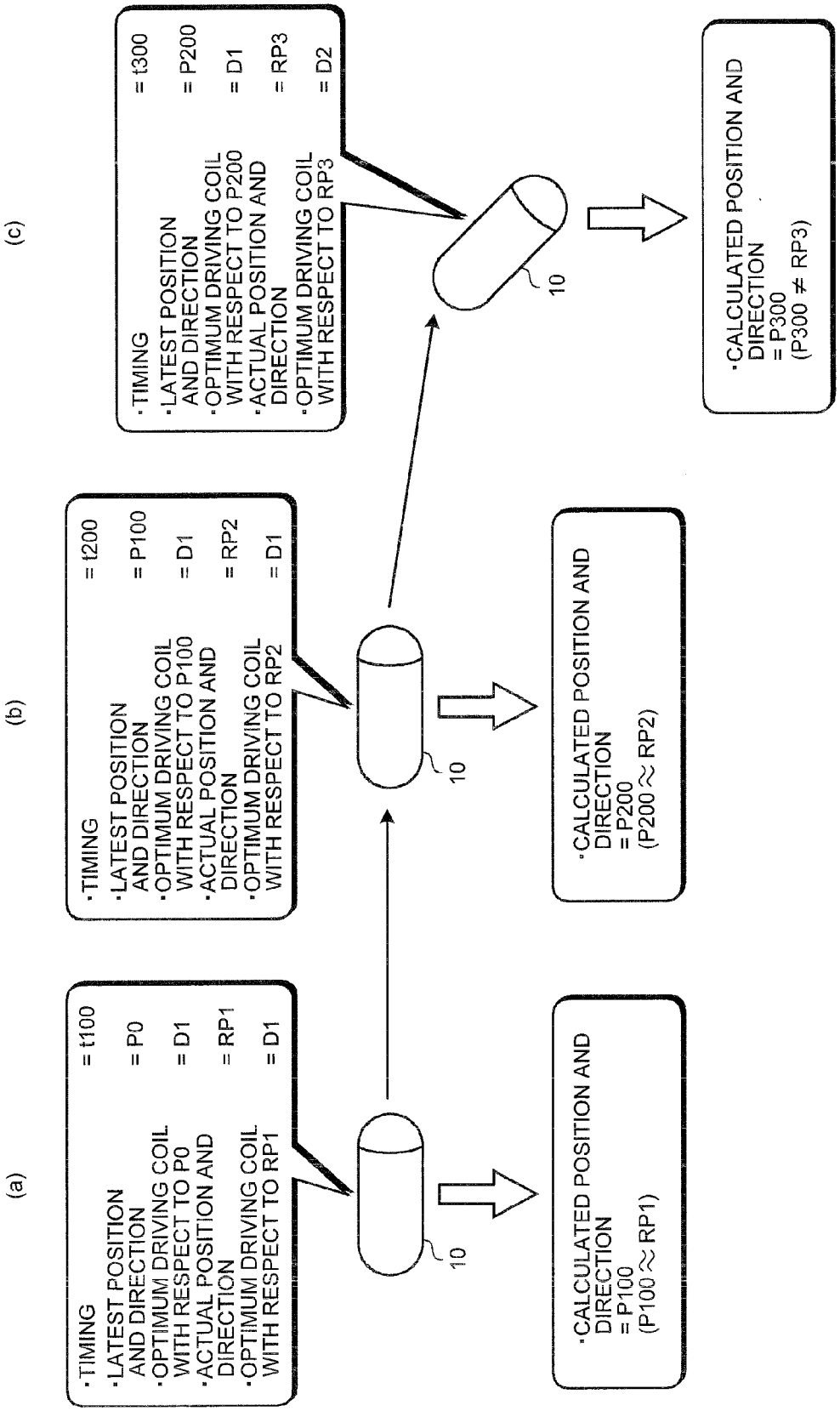

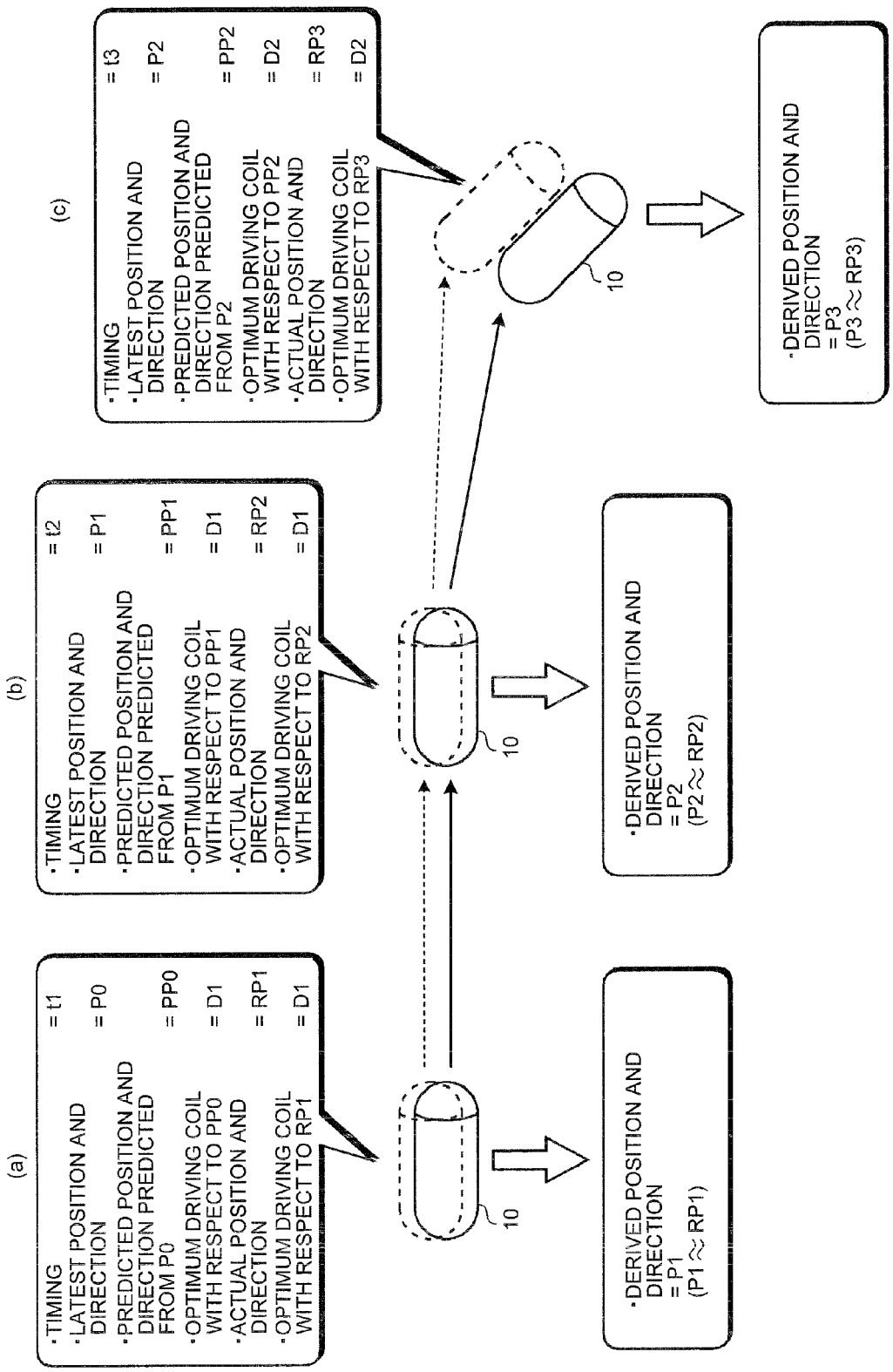

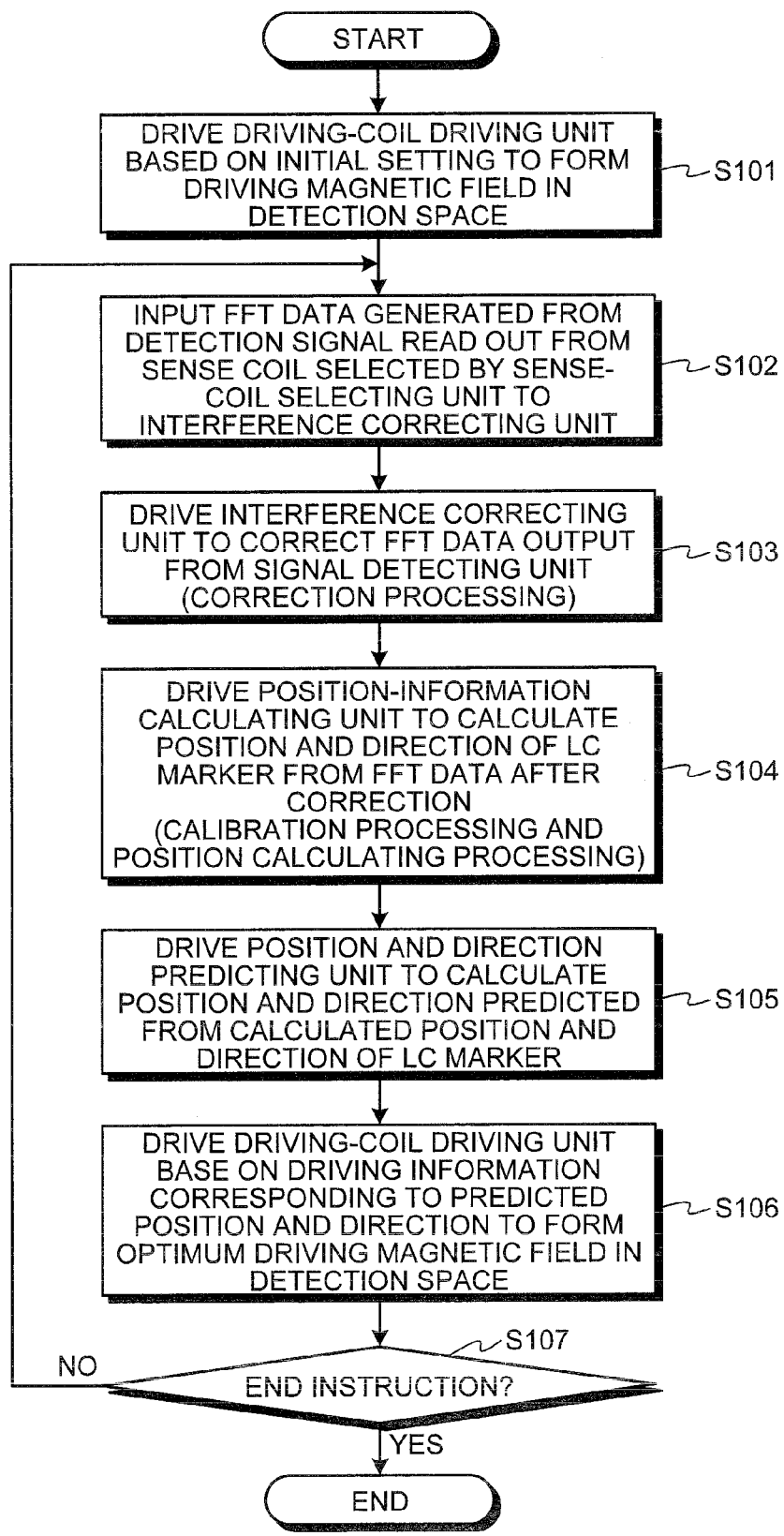

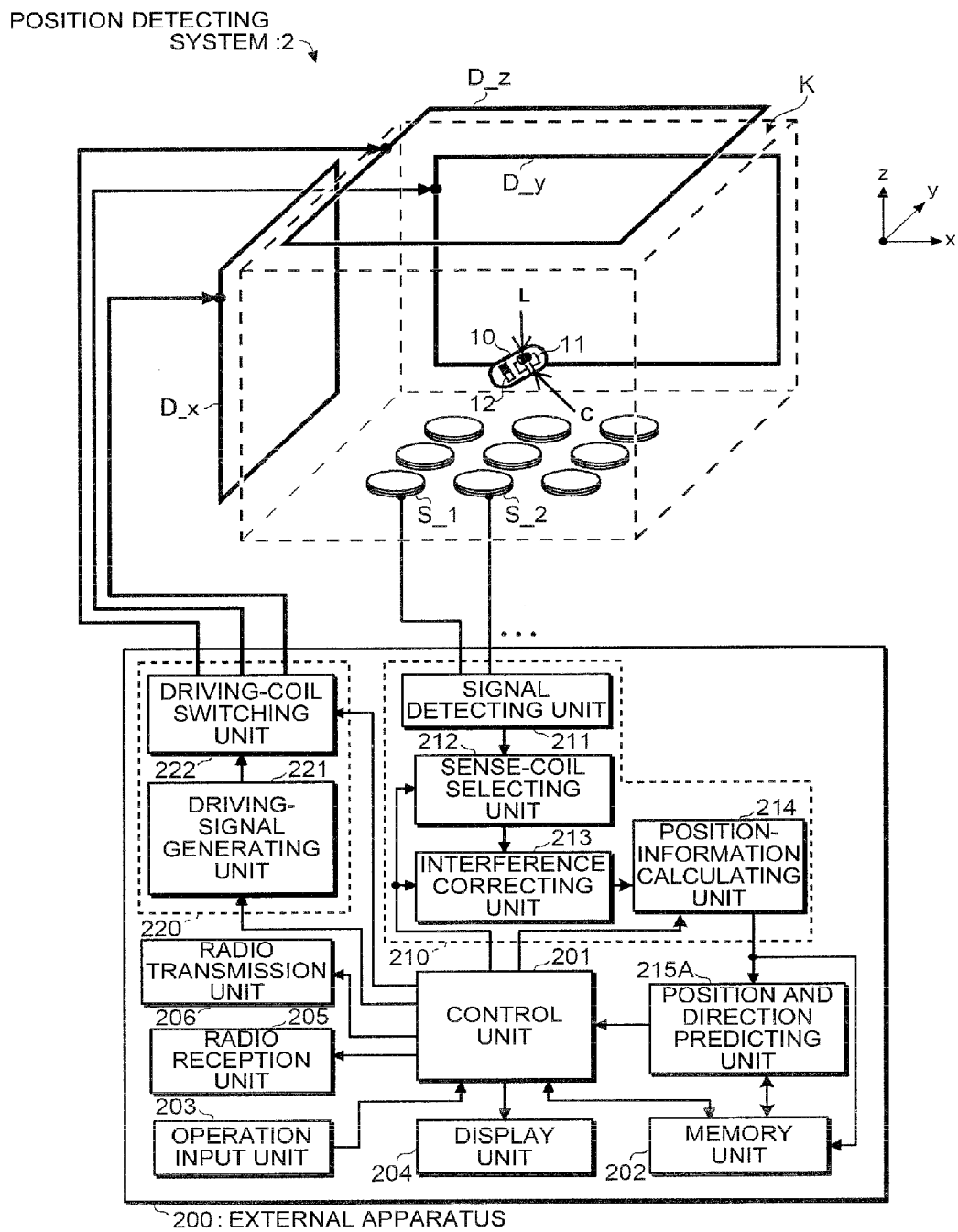

POSITION DETECTING SYSTEM AND POSITION DETECTING METHOD

CROSS-REFERENCE TO RELATED APPLICATIONS

This application is a continuation of PCT international application Ser. No. PCT/JP2010/050406 filed on Jan. 15, 2010 which designates the United States, incorporated herein by reference, and which claims the benefit of priority from Japanese Patent Application No. 2009-057018, filed on Mar. 10, 2009, incorporated herein by reference.

BACKGROUND OF THE INVENTION

1. Field of the Invention

The present invention relates to a position detecting system and a position detecting method, and, more particularly to a position detecting system and a position detecting method for detecting, using a magnetic field, the position of a body-insertable apparatus of a capsule type inserted into a subject.

2. Description of the Related Art

In recent years, body-insertable apparatuses such as a capsule endoscope are developed that are inserted into subjects such as a person and an animal and acquire various kinds of information such as images in the subjects and apply some treatment to the inside of the subjects (see, for example, Patent Documents 1 to 4 described below). For example, a body-insertable apparatus including an imaging device is inserted into a subject through the mouth, captures images of the inside of the subject, and transmits obtained images (hereinafter, "intra-subject images") to an external apparatus arranged on the outside of the subject by radio. An operator can diagnose a symptom and the like of the subject by visually checking the intra-subject images received by the external apparatus.

In a system including the body-insertable apparatus explained above, it is desired to accurately learn the position, the direction, and the like of the body-insertable apparatus for the purpose of, for example, imaging in the subject, identification of a treatment place, and position guidance for the body-insertable apparatus. Therefore, Japanese Laid-open Patent Publication No. 2007-175317 discloses a position detecting system in which a resonance circuit including a coil (L) and a capacitor (C) (hereinafter, "LC resonance circuit") is provided in a body-insertable apparatus and that detects, with a sense coil provided in an external apparatus, a resonant magnetic field generated by an alternating magnetic field given to the LC resonance circuit from the outside (hereinafter, "driving magnetic field") to detect the position and the direction of the body-insertable apparatus.

SUMMARY OF THE INVENTION

A position detecting system according to an aspect of the present invention includes a detected object that includes a magnetic-field generating unit that generates a magnetic field; at least one magnetic sensor that detects the magnetic field generated by the magnetic-field generating unit; a position detecting unit that calculates, based on a detection value of the magnetic sensor, at least one of a position and a direction of the detected object; a memory unit that stores a calculation result of the position detecting unit; a moving-amount calculating unit that calculates, based on results of the calculation at a plurality of times different from one another stored in the memory unit, a moving amount by which the detected object is predicted to move between first time when the position detecting unit calculates the at least one of the position and the direction of the detected object and second time after a predetermined time from the first time; a predicting unit that predicts, based on a calculation result of the position detecting unit at the first time stored in the memory unit and a calculation result of the moving-amount calculating unit, at least one of a position and a direction of the detected object at the second time; and a control unit that controls the position detecting system based on the at least one of the position and the direction of the detected object at the second time predicted by the predicting unit.

A position detecting system according to another aspect of the present invention includes a detected object having a magnetic-field generating unit that generates a magnetic field and a magnet; at least one magnetic sensor that detects the magnetic field generated by the magnetic-field generating unit; a position detecting unit that calculates, based on a detection value of the magnetic sensor, at least one of a position and a direction of the detected object; a guidance-magnetic-field generating unit that generates a guidance magnetic field acting on the magnet; a guidance-magnetic-field control unit that controls, based on guide information as information concerning any one of a position and a direction set as targets or both concerning the detected object, information concerning any one of target speed and target angular velocity or both, or information concerning any one of target acceleration and target angular acceleration or both, the guidance magnetic field generated by the guidance-magnetic-field generating unit; a memory unit that stores a calculation result of the position detecting unit; a moving-amount calculating unit that calculates, based on the guide information, a moving amount by which the detected object moves between first time when the position detecting unit calculates the at least one of the position and the direction of the detected object and second time after a predetermined time from the first time; a predicting unit that predicts, based on a calculation result of the position detecting unit at the first time stored in the memory unit and a calculation result of the moving-amount calculating unit, at least one of a position and a direction of the detected object at the second time; and a control unit that controls the position detecting unit based on the at least one of the position and the direction of the detected object at the second time predicted by the predicting unit.

A position detecting system according to still another aspect of the present invention includes a body-insertable apparatus that generates a resonant magnetic field induced by a driving magnetic field having a specific frequency; a driving-magnetic-field generating unit that generates the driving magnetic field having the specific frequency in a detection space in which a subject into which the body-insertable apparatus is inserted is surrounded; a magnetic sensor that detects a magnetic field generated in the detection space; a position detecting unit that detects, based on the magnetic field detected by the magnetic sensor, at least one of a position and a direction of the body-insertable apparatus; a guiding unit that guides the at least one of the position and the direction of the body-insertable apparatus to at least one of a position and a direction set as targets; a predicting unit that predicts, using the at least one of the position and the direction detected by the position detecting unit and guide information used by the guiding unit in guiding the body-insertable apparatus to the at least one of the position and the direction set as the targets, at least one of a position and a direction at certain time of the body-insertable apparatus; and a control unit that controls the driving-magnetic-field generating unit and the position detecting unit based on the at least one of the position and the direction at the certain time predicted by the predicting unit.

A position detecting system according to still another aspect of the present invention includes a body-insertable apparatus that generates a resonant magnetic field induced by a driving magnetic field having a specific frequency; a driving-magnetic-field generating unit that generates the driving magnetic field having the specific frequency in a detection space in which a subject into which the body-insertable apparatus is inserted is surrounded; a magnetic sensor that detects a magnetic field generated in the detection space; a position detecting unit that detects, based on the magnetic field detected by the magnetic sensor, at least one of a position and a direction of the body-insertable apparatus; a predicting unit that predicts, based on the at least one of the position and the direction at different time detected by the position detecting unit, at least one of a position and a direction at certain time of the body-insertable apparatus; and a control unit that controls the driving-magnetic-field generating unit and the position detecting unit based on the at least one of the position and the direction at the certain time predicted by the predicting unit.

A position detecting method according to an aspect of the present invention includes detecting, with at least one magnetic sensor, a magnetic field generated by a magnetic-field generating unit of a detected object having the magnetic-field generating unit that generates a magnetic field; performing, when a detection value of the magnetic sensor that detects the magnetic field is set as a true value and a detection value of the magnetic sensor predicted when it is assumed that the detected object is present in an estimation position is set as an estimation value, convergence calculation for changing the estimation position such that a difference between the true value and the estimation value is equal to or smaller than a predetermined value and calculates at least one of a position and a direction of the detected object; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and changing an initial value of the estimation position based on the predicted at least one of the position and the direction of the detected object at the second time.

A position detecting method according to another aspect of the present invention includes detecting, with at least one magnetic sensor among a plurality of magnetic sensors, a magnetic field generated by a magnetic-field generating unit of a detected object having the magnetic-field generating unit that generates a magnetic field; calculating, based on a detection value of the magnetic sensor, at least one of a position and a direction of the detected object; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and selecting, based on the predicted at least one of the position and the direction of the detected object at the second time, a magnetic sensor as a target of readout of the detection value out of the magnetic sensors.

A position detecting method according to still another aspect of the present invention includes detecting, with at least one magnetic sensor, a magnetic field generated by a magnetic-field generating unit of a detected object having the magnetic-field generating unit that generates a magnetic field; correcting the detection value by removing, from a detection value of the magnetic sensor that detects the magnetic field, a component of an interference magnetic field, which is caused when a coil arranged near the magnetic-field generating unit is induced by the magnetic field, in the detection value and calculating, based on the detection value after the correction, at least one of a position and a direction of the detected object; calculating, based on a detection value of the magnetic sensor, at least one of a position and a direction of the detected object; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and changing, based on the predicted at least one of the position and the direction of the detected object at the second time, the component of the interference magnetic field that should be removed from the detection value of the magnetic sensor.

A position detecting method according to still another aspect of the present invention includes supplying a driving signal to a driving coil to generate a driving magnetic field having a specific frequency; detecting, with at least one magnetic sensor, a magnetic field generated in the driving magnetic field by a magnetic-field generating unit of a detected object including the magnetic-field generating unit, the magnetic-field generating unit including a resonance circuit that generates a resonant magnetic field induced by the driving magnetic field; calculating, based on a detection value the magnetic sensor that detects the magnetic field, at least one of a position and a direction of the detected object; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and changing the driving signal based on the predicted at least one of the position and the direction of the detected object at the second time.

A position detecting method according to still another aspect of the present invention includes detecting, with at least one magnetic sensor, a magnetic field generated by a magnetic-field generating unit of a detected object having the magnetic-field generating unit that generates a magnetic field and a magnet; performing, when a detection value of the magnetic sensor that detects the magnetic field is set as a true value and a detection value of the magnetic sensor predicted when it is assumed that the detected object is present in an estimation position is set as an estimation value, convergence calculation for changing the estimation position such that a difference between the true value and the estimation value is equal to or smaller than a predetermined value and calculates at least one of a position and a direction of the detected object; generating, based on guide information as information concerning any one of a position and a direction set as targets or both concerning the detected object, information concerning any one of target speed and target angular velocity or both, or information concerning any one of target acceleration and target angular acceleration or both, a guidance magnetic field acting on the magnet; guiding, with the guidance magnetic field, at least one of a position and a direction of the detected object to at least one of a position and a direction set as targets; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and changing an initial value of the estimation position based on the predicted at least one of the position and the direction of the detected object at the second time.

A position detecting method according to still another aspect of the present invention includes detecting, with at least one magnetic sensor among a plurality of magnetic sensors, a magnetic field generated by a magnetic-field generating unit of a detected object having the magnetic-field generating unit that generates a magnetic field and a magnet; calculating, based on a detection value of the magnetic sensor that detects the magnetic field, at least one of a position and a direction of the detected object; generating, based on guide information as information concerning any one of a position and a direction set as targets or both concerning the detected object, information concerning any one of target speed and target angular velocity or both, or information concerning any one of target acceleration and target angular acceleration or both, a guidance magnetic field acting on the magnet; guiding, with the guidance magnetic field, at least one of a position and a direction of the detected object to at least one of a position and a direction set as targets; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and selecting, based on the predicted at least one of the position and the direction of the detected object at the second time, a magnetic sensor as a target of readout of the detection value out of the magnetic sensors.

A position detecting method according to still another aspect of the present invention includes detecting, with at least one magnetic sensor, a magnetic field generated by a magnetic-field generating unit of a detected object having the magnetic-field generating unit that generates a magnetic field and a magnet; correcting the detection value by removing, from a detection value of the magnetic sensor that detects the magnetic field, a component of an interference magnetic field, which is caused when a coil arranged near the magnetic-field generating unit is induced by the magnetic field, in the detection value and calculating, based on the detection value after the correction, at least one of a position and a direction of the detected object; generating, based on guide information as information concerning any one of a position and a direction set as targets or both concerning the detected object, information concerning any one of target speed and target angular velocity or both, or information concerning any one of target acceleration and target angular acceleration or both, a guidance magnetic field acting on the magnet; guiding, with the guidance magnetic field, at least one of a position and a direction of the detected object to at least one of a position and a direction set as targets; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and changing, based on the predicted at least one of the position and the direction of the detected object at the second time, the component of the interference magnetic field that should be removed from the detection value of the magnetic sensor.

A position detecting method according to still another aspect of the present invention includes supplying a driving signal to a driving coil to generate a driving magnetic field having a specific frequency; detecting, with at least one magnetic sensor, a magnetic field generated in the driving magnetic field by a magnetic-field generating unit of a detected object including the magnetic-field generating unit and a magnet, the magnetic-field generating unit including a resonance circuit that generates a resonant magnetic field induced by the driving magnetic field; generating, based on guide information as information concerning any one of a position and a direction set as targets or both concerning the detected object, information concerning any one of target speed and target angular velocity or both, or information concerning any one of target acceleration and target angular acceleration or both, a guidance magnetic field acting on the magnet; guiding, with the guidance magnetic field, at least one of a position and a direction of the detected object to at least one of a position and a direction set as targets; calculating a moving amount by which the detected object is predicted to move between first time when the at least one of the position and the direction of the detected object is calculated and second time after a predetermined time from the first time; predicting, based on a result of the calculation performed at the first time and a result of the calculation of the moving amount, at least one of a position and a direction of the detected object at the second time; and changing the driving signal based on the predicted at least one of the position and the direction of the detected object at the second time.

A position detecting method according to still another aspect of the present invention is for detecting, with a position detecting system including a guiding unit that guides at least one of a position and a direction of a body-insertable apparatus that generates a resonant magnetic field induced by a driving magnetic field having a specific frequency to at least one of a position and a direction set as targets, at least one of a position and a direction of the body-insertable apparatus. The position detecting method includes generating the driving magnetic field having the specific frequency in a detection space in which a subject into which the body-insertable apparatus is inserted is surrounded; generating the resonant magnetic field from the body-insertable apparatus with the driving magnetic field having the specific frequency; detecting a magnetic field generated in the detection space; calculating, based on the detected magnetic field, at least one of a position and a direction of the body-insertable apparatus; predicting, using the calculated at least one of the position and the direction and guide information used by the guiding unit in guiding the body-insertable apparatus to the at least one of the position and the direction set as the targets, at least one of a position and a direction at certain time of the body-insertable apparatus; and controlling the driving magnetic field based on the predicted at least one of the position and the direction at the certain time.

A position detecting method according to still another aspect of the present invention is for detecting, with a position detecting system, at least one of a position and a direction of a body-insertable apparatus that generates a resonant magnetic field induced by a driving magnetic field having a specific frequency. The position detecting method includes generating the driving magnetic field having the specific frequency in a detection space in which a subject into which the body-insertable apparatus is inserted is surrounded; generating the resonant magnetic field from the body-insertable apparatus with the driving magnetic field having the specific frequency; detecting a magnetic field generated in the detection space; detecting, based on the detected magnetic field, at least one of a position and a direction of the body-insertable apparatus; predicting, based on the detected at least one of the position and the direction at different time, at least one of a position and a direction at certain time of the body-insertable apparatus; and controlling the driving magnetic field based on the predicted at least one of the position and the direction at the certain time.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a diagram for explaining formation of a driving magnetic field in a detection space based on a position detection result calculated immediately before the formation;

FIG. 6 is a diagram for explaining formation of a driving magnetic field in the detection space based on predicted position and direction;

FIG. 7 is a flowchart for explaining an overview of position detection processing according to the first or second embodiment of the present invention; and FIG. 8 is a schematic diagram of a schematic configuration of a position detecting system according to the second embodiment of the present invention.

DETAILED DESCRIPTION OF THE PREFERRED EMBODIMENTS

Exemplary embodiments of the present invention are explained in detail below with reference to the accompanying drawings. In the following explanation, in the figures, shapes, sizes, and positional relations are merely schematically shown enough for understanding the contents of the present invention. Therefore, the present invention is not limited to only the shapes, the sizes, and the positional relations shown in the figures. In the figures, a part of hatching in a section is omitted for clarification of a configuration. Numerical values described below are merely preferred examples in the present invention. Therefore, the present invention is not limited to the numerical values described as the examples.

First Embodiment

The configuration and the operation of a position-detecting magnetic guidance system 1 according to a first embodiment of the present invention are explained in detail below with reference to the accompanying drawings.

Configuration of Position Detecting System

Figure 1:
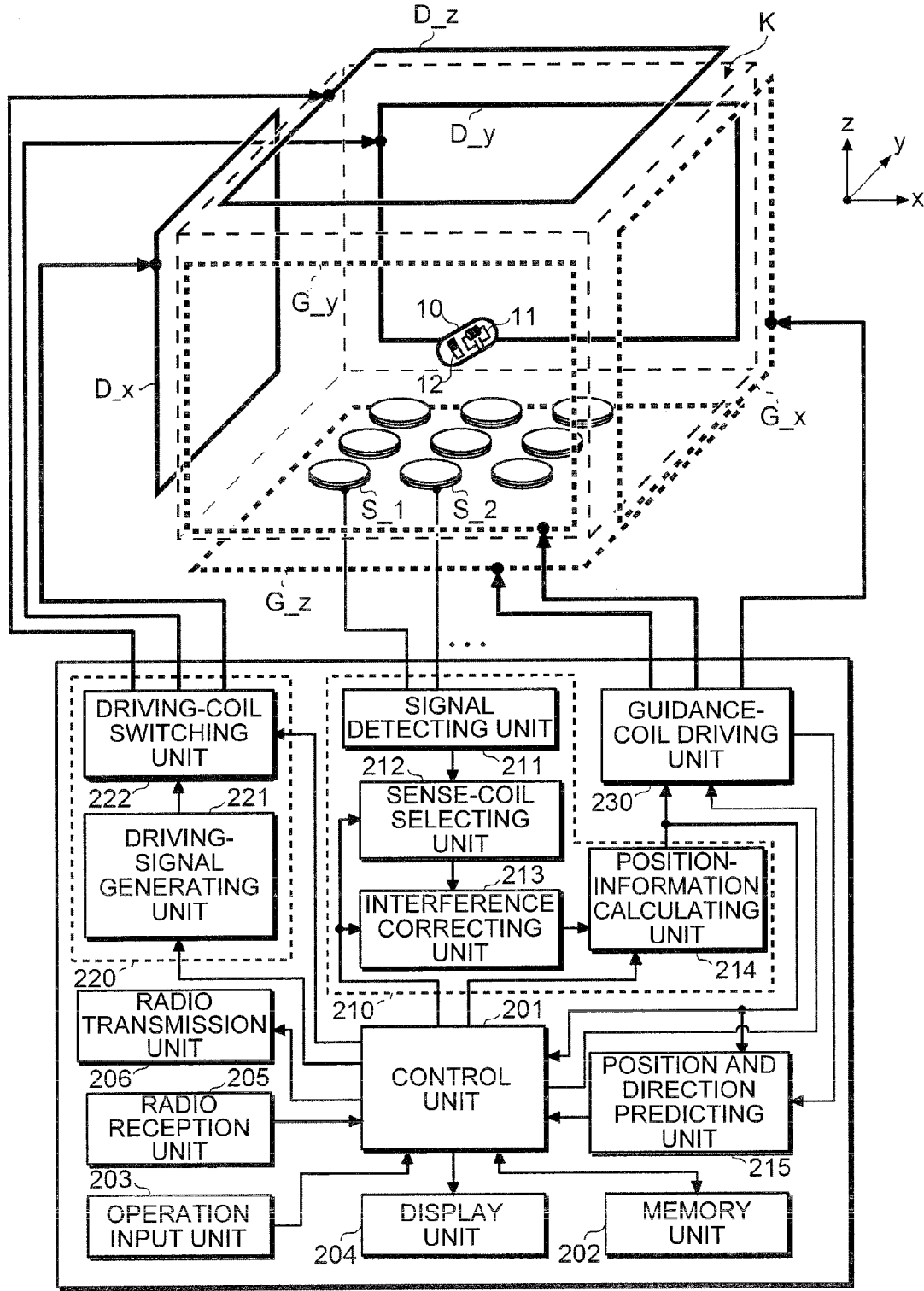
FIG. 1 is a schematic diagram of a schematic configuration of a position-detecting magnetic guidance system according to a first embodiment of the present invention.

FIG. 1 is a schematic diagram of a schematic configuration of the position detecting system 1 according to this embodiment. As shown in FIG. 1, the position detecting system 1 includes a detection space K in which a subject into which an LC marker 10 as a body-insertable apparatus is inserted is surrounded and an external apparatus 200 that detects the position and the direction (also referred to as the posture and the direction) of the LC marker 10 in the detection space K. The LC marker 10 is equivalent to a detected object.

LC Marker

As shown in FIG. 1, the LC marker 10 includes a resonant-magnetic-field generating unit 11 (see FIG. 1) that generates a resonant magnetic field for position detection. The resonant-magnetic-field generating unit 11 includes an LC resonance circuit including a capacitor (C) and an inductor (L) connected in parallel. The resonant-magnetic-field generating unit 11 excites the LC resonance circuit with a magnetic field for position detection having a specific frequency and a magnetic field for position detection (hereinafter, "driving magnetic field") having a frequency substantially equal to, for example, a resonant frequency F0 to generate a resonant magnetic field having a frequency equal to that of the driving magnetic field. The resonant frequency F0 is a resonant frequency of the LC resonance circuit determined by the capacitor (C) and the inductor (L) connected in parallel.

Figure 2:
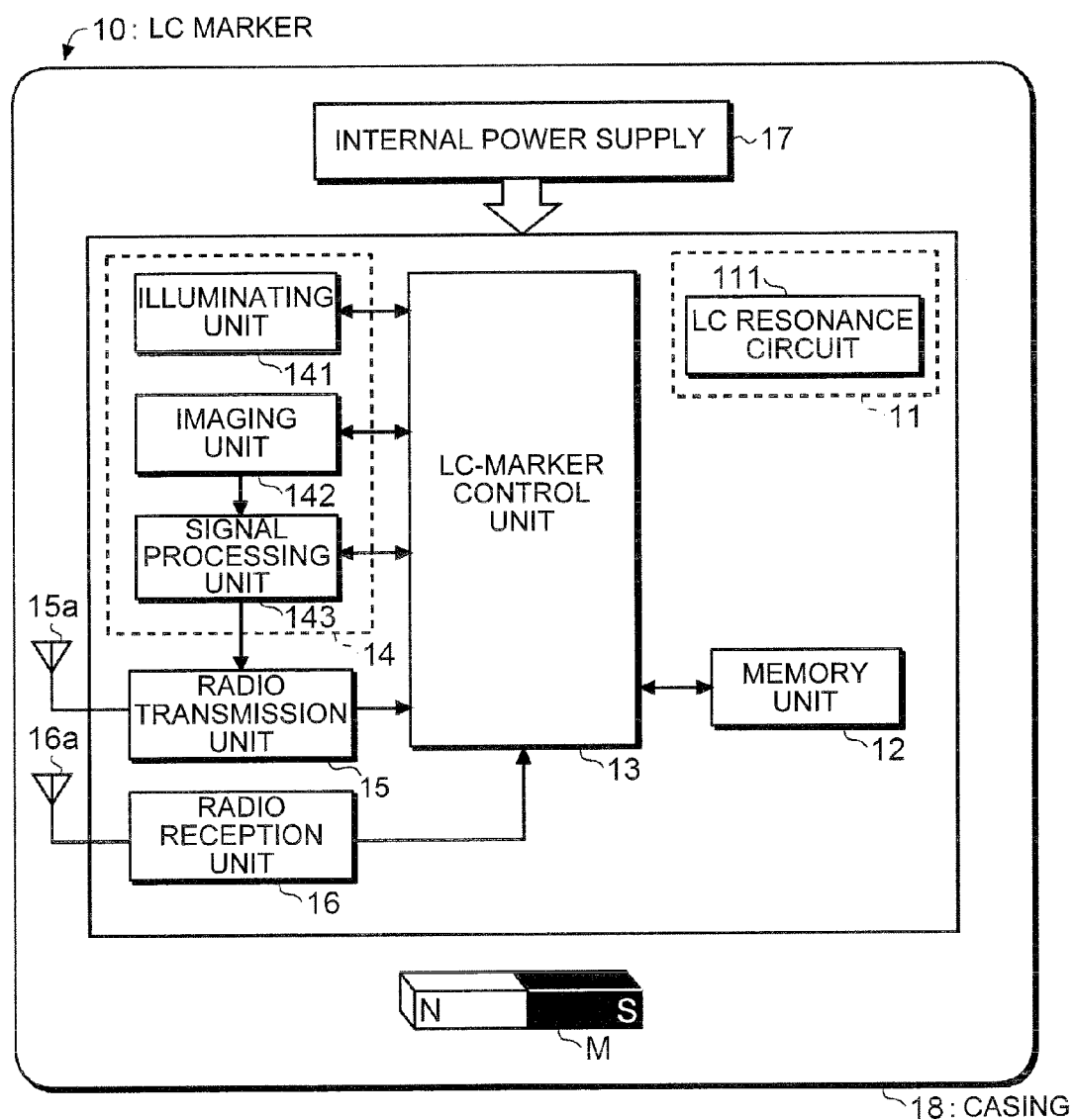
FIG. 2 is a block diagram of a schematic configuration example of an LC marker according to the first embodiment or a second embodiment of the present invention.

The LC marker 10 can have a function of, for example, a capsule-type medical apparatus. In this case, the LC marker 10 includes, as shown in FIG. 2, for example, an LC resonance circuit 111, an LC-marker control unit 13 that controls units in the LC marker 10, a memory unit 12 that stores various computer programs executed by the LC-marker control unit 13, intra-subject information acquired by an intra-subject-information acquiring unit 14, and the like, the intra-subject-information acquiring unit 14 that acquires various kinds of information in the subject, a radio transmission unit 15 and a transmission antenna 15a that transmit the intra-subject information acquired by the intra-subject-information acquiring unit 14 to the outside of the LC marker 10 as a radio signal, a radio reception unit 16 and a reception antenna 16a that receive various operation instructions and the like transmitted from an external apparatus 200 as radio signals, and an internal power supply 17 that supplies electric power to the units of the LC marker 10. FIG. 2 is a block diagram of a schematic configuration example of the LC marker 10 according to this embodiment.

In the configuration, the intra-subject-information acquiring unit 14 includes, for example, an imaging unit 142 that acquires an image in the subject as intra-subject information, an illuminating unit 141 that illuminates the inside of the subject when the imaging unit 142 captures an image of the inside of the subject, and a signal processing unit 143 that executes predetermined signal processing on the intra-subject image acquired by the imaging unit 142.

Figure 3:
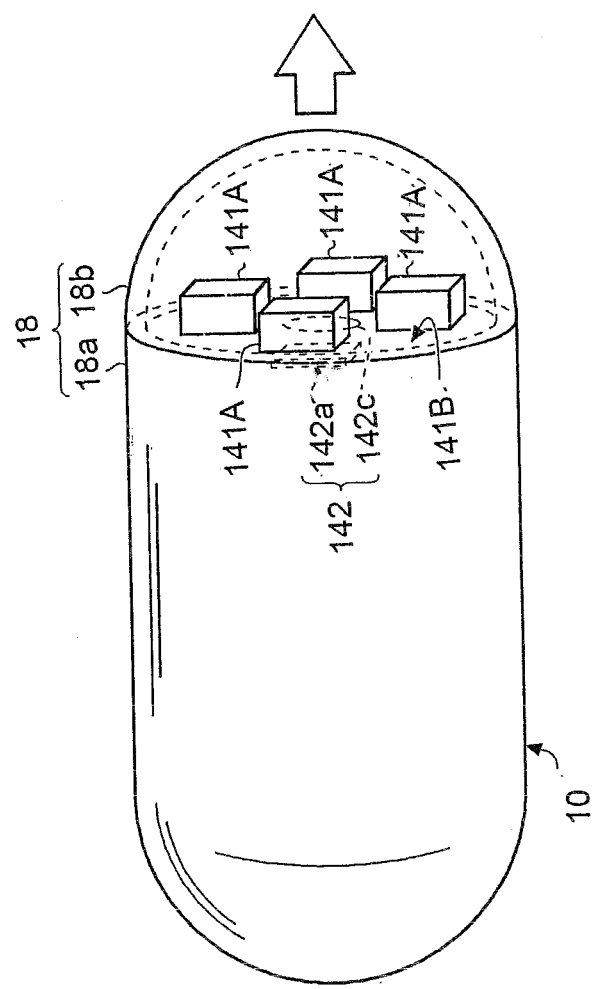
FIG. 3 is an external view of the schematic configuration example of the LC marker according to the first or second embodiment of the present invention.

For example, as shown in FIG. 3, the imaging unit 142 includes an imaging device 142a that converts incident light into an electric signal and forms an image, an object lens 142c disposed on a light receiving surface side of the imaging device 142a, and a not-shown imaging-device driving circuit that drives the imaging device 142a. FIG. 3 is an external view of a schematic configuration example of the LC marker 10 according to this embodiment.

As shown in FIG. 3, as the imaging device 142a, for example, a charge coupled device (CCD) camera or a complementary metal oxide semiconductor (CMOS) camera can be used. The imaging-device driving circuit drives the imaging device 142a and acquires an intra-subject image of an analog signal under the control by the LC-marker control unit 13. The imaging-device driving circuit outputs the intra-subject image of the analog signal, which is read out from the imaging device 142*a*, to the signal processing unit 143.

As shown in FIG. 3, the illuminating unit 141 includes a plurality of light sources 141A and a not-shown light-source driving circuit that drives the light sources 141A. As the light sources 141A, for example, light emitting diodes (LEDs) can be used. The light-source driving circuit drives the light sources 141A according to the driving of the imaging unit 142 to illuminate the inside of the subject under the control by the LC-marker control unit 13.

The LC marker 10 includes a permanent magnet M. The permanent magnet M is fixed to a housing 18 of the LC marker 10. Therefore, because a magnetic field generated in the detection space K for the purpose of guiding the position and the direction of the LC marker 10 itself according to the position and the direction of a moving target (hereinafter, "guidance magnetic field") acts on the permanent magnet M of the LC marker 10, it is possible to control the position and the direction of the LC marker 10 from the outside.

The units (11, 12, 13, 14, 15, 15*a*, 16, 16*a*, 17, and M) are surrounded in the housing 18 of, for example, a capsule type. For example, as shown in FIG. 3, the housing 18 includes a container 18*a*, one end of which is formed in a semicircular dome shape and the other end of which is formed in an opened substantially cylindrical shape or semielliptical spherical shape, and a cap 18*b* that is fit in the opening of the container 18*a* to seal the inside of the housing 18. The housing 18 has, for example, size small enough for the subject to swallow. In this embodiment, at least the cap 18*b* is formed of a transparent material. The light sources 141A are mounted on a circuit board 141B mounted with the light-source driving circuit (not shown). Similarly, the imaging device 142*a* and the object lens 142*c* are mounted on a circuit board (not shown) mounted with the imaging-device driving circuit (not shown). The circuit board 141B mounted with the light sources 141A and the circuit board mounted with the imaging device 142*a* are arranged on the transparent cap 18*b* side in the housing 18. In this case, device mounting surfaces in the circuit boards are faced to the cap 18*b* side. Therefore, as shown in FIG. 3, an imaging and illuminating direction of the imaging device 142*a* and the light sources 141A is faced to the outside of the LC marker 10 via the transparent cap 18*b*.

Detection Space

Referring back to FIG. 1, the detection space K has disposed therein driving coils D_x, D_y, and D_z (in the following explanation, reference sign of an arbitrary driving coil is D) that generate substantially uniform driving magnetic fields in different directions in the detection space K, guidance coils G_x, G_y, and G_z (in the following explanation, reference sign of an arbitrary guidance coil is G) that generate guidance magnetisms in different directions in the detection space K, and a plurality of sense coils S_1, S_2, and the like (in the following explanation, reference sign of an arbitrary sense coil is S) that detect a resonant magnetic field generated by the LC resonance circuit 111 of the LC marker 10.

The driving coils D_x, D_y, and D_z respectively form pairs with not-shown driving coils opposed thereto across the detection space K and generate substantially uniform driving magnetic fields in the detection space K. For example, the driving coil D_x and the driving coil forming the pair with the driving coil D_x generate driving magnetic fields of substantially uniform lines of magnetic force in an x-axis direction in the detection space K. Similarly, the driving coil D_y and the driving coil forming the pair with the driving coil D_y generate driving magnetic fields of substantially uniform lines of magnetic force in a y-axis direction in the detection space K. The driving coil D_z and the driving coil forming the pair with the driving coil D_z generate driving magnetic fields of substantially uniform lines of magnetic force in a z-axis direction in the detection space K. However, the present invention is not limited to this. Driving coils that generate driving magnetic fields of lines of magnetic forces not parallel to the x-axis, the y-axis, and the z-axis can be provided. In the following explanation, for simplification of explanation, attention is paid to the driving coils D shown in the figure.

As explained above, because the driving coils D that can generate driving magnetic fields in different directions are provided, it is possible to select and drive, according to the position and the direction of the LC marker 10, the driving coil D that generates an optimum driving magnetic field. As a result, irrespective of which direction the LC resonance circuit 111 (in particular, the inductor (L)) of the LC marker 10 faces in the detection space K, it is possible to cause the LC resonance circuit 111 to generate a resonant magnetic field having stable intensity. This makes it possible to improve position detection accuracy of the LC marker 10.

The guidance coils G_x, G_y, and G_z respectively form pairs with not-shown guidance coils opposed thereto across the detection space K. The guidance coils G_x, G_y, and G_z respectively generate, in the detection space K, guidance magnetic fields for guiding the LC marker 10 to target positions and directions according to the position and the direction of the LC marker 10 (in particular, the permanent magnet M). In the following explanation, for simplification of explanation, attention is paid to the guidance coils G shown in the figure.

The sense coils S are magnetic sensors including coils that can detect, for example, the intensity and the direction of a magnetic field in the y-axis direction. However, the present invention is not limited to this. The sense coils S can be configured by using magnetic sensors including, for example, magnetic resistance elements or magnetic impedance elements (MI elements). The sense coils S can also include two-axis or three-axis magnetic sensors that detect magnetic field intensities in at least two axis directions among the x-axis, the y-axis, and the z-axis.

The sense coils S are mounted on, for example, a not-shown circuit board disposed in the detection space K or near the detection space K. The circuit board is arranged in a position where the circuit board is less easily affected by a magnetic field generated by at least one of the driving coils D and the guidance coils G and a resonant magnetic field generated by the LC resonance circuit 111 can be easily input. Consequently, because the influence of an unnecessary magnetic field is reduced, it is possible to calculate accurate position and direction of the LC marker 10. For example, the circuit board is fixed on the lower side of a placing table (not shown) for placing the subject into which the LC marker 10 is inserted (see FIG. 1) or fixed to the ceiling above the detection space K.

External Apparatus

The external apparatus 200 includes a driving-coil driving unit 220 that outputs a signal used for driving of the driving coils D (hereinafter, "driving signal"), a guidance-coil driving unit 230 that outputs a signal used for driving of the guidance coils G (hereinafter, "guidance signal"), a position detecting unit 210 that calculates information concerning the position and the direction of the LC marker 10 (hereinafter simply referred to as "position and direction") from voltage changes read out from the sense coils S (hereinafter, "detection signal"), a control unit 201 that controls units in the external apparatus 200, a memory unit 202 that stores various computer programs, parameters, and the like executed when the control unit 201 controls the units, an operation input unit 203 with which an operator inputs various operation instructions for the LC marker 10 and a position and a direction set as guidance targets of the LC marker 10, a display unit 204 that displays, as an image (including a video) and sound, the position and the direction of the LC marker 10 calculated by the position detecting unit 210 and intra-subject information acquired from the LC marker 10, a radio reception unit 205 that receives the intra-subject information and the like transmitted from the LC marker 10 as a radio signal, and a radio transmission unit 206 that transmits the various operation instructions such as an imaging instruction to the LC marker 10 as a radio signal.

The external apparatus 200 further includes position and direction predicting unit 215 as a predicting unit that predicts a position and a direction at certain time (also referred to as timing) of the LC marker 10 from the position and the direction of the LC marker 10 calculated by the position detecting unit 210 and guide information (equivalent to guidance information explained later) with which the guidance-coil driving unit 230 guides the LC marker 10 using the guidance coils G.

The control unit 201 includes, for example, a CPU or a MPU and controls the units in the external apparatus 200 according to the computer programs and the parameters read out from the memory unit 202. The memory unit 202 includes, for example, a RAM or a ROM and stores the computer programs and the parameters executed when the control unit 201 controls the units. The intra-subject information received from the LC marker 10 and the information such as the position and the direction of the LC marker 10 calculated by the position detecting unit 210 are stored in the memory unit 202 as appropriate.

Driving information, a correction amount, calibration information, and guidance information explained later are stored in the memory unit 202 as appropriate. The driving information is managed in the memory unit 202 in association with, for example, the position and the direction. The correction amount is managed in the memory unit 202 in association with, for example, the position and the direction. The calibration information is managed in the memory unit 202 in association with, for example, the driving information. The guidance information is managed in the memory unit 202 in association with, for example, the position and the direction.

Further, in the memory unit 202, the position and the direction of the LC marker 10 can be managed in association with information concerning a resonant magnetic field explained later. This makes it possible to easily and quickly calculate the position and the direction of the LC marker 10 from information concerning a resonant magnetic field extracted by calibration processing explained later. However, the present invention is not limited to this. The position and the direction of the LC marker 10 can be sequentially calculated from the extracted information concerning the resonant magnetic field.

The operation input unit 203 includes, for example, a keyboard, a mouse, a ten key, or a joy stick. The operation input unit 203 is used by the operator to input various operation instructions for the LC marker 10 such as an imaging instruction (including other intra-subject information acquisition instructions), a position and a direction set as guidance targets of the LC marker 10, a screen switching instruction for switching a screen displayed on the display unit 204, and the like. A function of switching a screen displayed on the display unit 204 is effective when the LC marker 10 includes a plurality of the imaging unit 142.

The display unit 204 includes a display device such as a liquid crystal display, a plasma display, or an LED array. The display unit 204 displays information such as the position and the direction of the LC marker 10 and intra-subject information such as an intra-subject image transmitted from the LC marker 10. A function of reproducing sound using a speaker or the like can be mounted on the display unit 204. The display unit 204 informs the operator of various kinds of operation guidance and information concerning the remaining battery power of the LC marker 10 and the like (including warning) by sound using this sound reproducing function.

The radio reception unit 205 is connected to a not-shown reception antenna including a dipole antenna arranged near the detection space K. The reception antenna is arranged, for example, near the detection space K. The radio reception unit 205 receives an intra-subject image or the like transmitted from the LC marker 10 as a radio signal via the reception antenna and, after executing various kinds of processing such as filtering, down-convert, demodulation, and decoding on the received signal, outputs the signal to the control unit 201.

The radio transmission unit 206 is connected to a not-shown transmission antenna including a dipole antenna arranged near the detection space K. The transmission antenna is arranged, for example, near the detection space K. After executing various kinds of processing such as superimposition on a reference frequency signal for transmission, modulation, and up-convert on a signal of various operation instructions or the like for the LC marker 10 input from the control unit 201, the radio transmission unit 206 transmits the signal from the transmission antenna to the LC marker 10 as a radio wave signal.

The driving-coil driving unit 220 and the driving coils D shown in FIG. 1 function as a driving-magnetic-field generating unit that generates a driving magnetic field for position detection in the detection space K. The driving-coil driving unit 220 includes, for example, a driving-signal generating unit 221 that generates a driving signal and a driving-coil switching unit 222 as a switching unit that switches the driving coil D at an input destination of the driving signal to any one of the driving coils D.

The driving-signal generating unit 221 calculates, for example, according to a control signal input from the control unit 201, a signal waveform having a frequency substantially equal to the resonant frequency F0 of the LC resonance circuit 111 in the LC marker 10 and generates a driving signal having a frequency substantially equal to the resonant frequency F0 using the signal waveform. After current-amplifying the generated driving signal, the driving-signal generating unit 221 outputs the driving signal after the amplification to the driving-coil switching unit 222.

The driving-coil switching unit 222 switches, under the control by the control unit 201, an input destination of the driving signal to any driving coils D forming the pair out of the driving coils D. When the driving signal output from the driving-signal generating unit 221 is input to the driving coils D selected in this way, an optimum driving magnetic field for exciting the LC resonance circuit 111 is generated in the detection space K.

The control unit 201 controls to drive the driving-coil switching unit 222 based on the position and the direction of the LC marker 10 predicted by the position and direction predicting unit 215 explained later (hereinafter, "predicted position and direction"). In other words, the control unit 201 switches, based on the predicted position and direction, information for controlling to drive the driving-coil switching unit 222 (equivalent to driving information explained later) and controls to drive the driving-coil driving unit 220 according to the driving information. Consequently, the driving coils D that can generate an optimum driving magnetic field when the LC marker 10 is in the predicted position and direction are selected and the driving signal is input to the driving coils D. This makes it possible to generate an optimum driving magnetic field in the detection space K. The driving information is identification information of the driving coils D driven when a driving magnetic field is generated and information concerning an amplitude value, a phase, and the like of a driving signal input to the driving coils D.

The sense coils S and the position detecting unit 210 shown in FIG. 1 calculate the position and the direction of the LC marker 10 using a resonant magnetic field generated by the LC marker 10 according to a driving magnetic field generated by the driving-magnetic-field generating unit including the driving coils D and the driving-coil driving unit 220. The position detecting unit 210 includes, for example, a signal detecting unit 211, a sense-coil selecting unit 212 as a selecting unit that selects a magnetic sensor used for readout of a magnetic field, an interference correcting unit 213, and a position-information calculating unit 214.

The sense-coil selecting unit 212 selects, for example, under the control by the control unit 201, the sense coil S set as a readout target of a detection signal by the signal detecting unit 211 out of the sensor coils S. The control unit 201 also has a function of a selection control unit that controls the sense-coil selecting unit 212. The control unit 201 controls the sense-coil selecting unit 212 such that, for example, a detection signal from one or more sense coils S set as readout targets among the sense coils 1 two-dimensionally arrayed.

The signal detecting unit 211 reads out, periodically or non-periodically, voltage changes occurred in the sense coils S as detection signals and execute processing such as amplification, band limitation, A/D conversion, and fast Fourier transform (FFT) on the read-out detection signal as appropriate to generate data indicating information concerning a magnetic field input to the selected sense coils 1 (hereinafter, "FFT data" or "detection value"). The detection signals read out from the sense coils S are signals representing, as changes in voltage, magnetic field information such as the intensities, phases, and the like of magnetic fields in positions where the sense coils S are arranged. The FFT data is data obtained by converting magnetic field information included in the detection signals read out from the sense coils S into information including components of intensities and phases. The FFT data generated in this way is, for example, input to the interference correcting unit 213 via the sense-coil selecting unit 212.

The interference correcting unit 213 removes, from the FFT data input via the sense-coil selecting unit 212, magnetic field components other than a resonant magnetic field, i.e., components (also referred to as "information") of unnecessary magnetic fields such as an interference magnetic field included in the FFT data.

The unnecessary magnetic fields included in the FFT data include a magnetic field (an interference magnetic field), which has a phase difference of about 180° with respect to the resonant magnetic field, caused when the coils (the driving coils D, the guidance coils G, etc.) arranged near the detection space K are interfered by the resonant magnetic field from the LC resonance circuit 111. In this embodiment, the components of the unnecessary magnetic fields are removed from the FFT data using a correction amount corresponding to the predicted position and direction input to the control unit 201 from the position-information calculating unit 214 immediately before the removal. This is referred to as correction processing below.

The correction amount can be acquired by, for example, providing current detecting units respectively in the driving coils D and the guidance coils G and simulating, from current values detected by the current detecting units, information concerning interference magnetic fields respectively generated by the driving coils D and the guidance coils G (which is FFT data) or calculating the information according to actual measurement. The acquired correction amount is registered in a look-up table (LUT) or the like, for example, the memory unit 202 in association with a position and a direction.

In the correction processing during position detection, the control unit 201 refers to the LUT in the memory unit 202 using a position and a direction input from the position-information calculating unit 214 immediately before the correction processing (i.e., the last position and direction) to acquire a correction amount associated with the position and the direction input from the position-information calculating unit 214 last time and inputs the correction amount to the interference correcting unit 213. The interference correcting unit 213 executes the correction processing using the FFT data input via the sense-coil selecting unit 212 and the correction amount input from the control unit 201 to remove components of the interference magnetic fields from the FFT data.

However, the present invention is not limited to this. It is also possible to register parameters for correction corresponding to positions and directions in the LUT in advance and refer to the LUT using the predicted position and direction as appropriate to calculate a position and a direction from the FFT data using the acquired parameters for correction.

The FFT data corrected as explained above is input to the position-information calculating unit 214. The position-information calculating unit 214 executes predetermined arithmetic processing on the input FFT data after the correction to calculate the position and the direction of the LC marker 10 from the FFT data after the correction. This processing is referred to as position calculating processing below.

Figure 4:
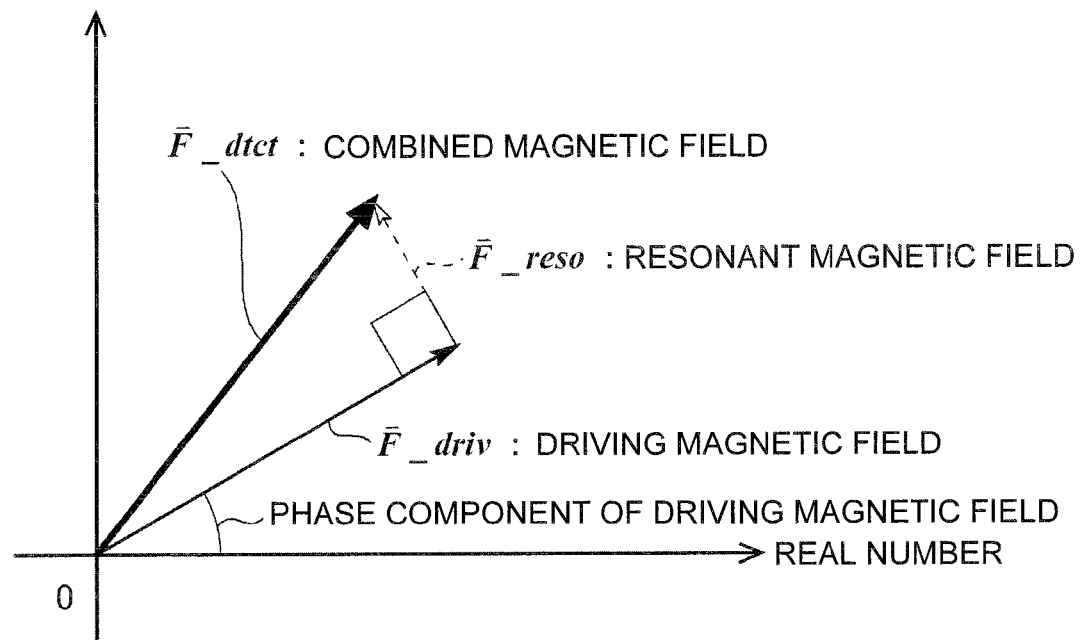
FIG. 4 is a diagram for explaining a relation among a driving magnetic field, a combined magnetic field, and an induced magnetic field in the first or second embodiment of the present invention.

The FFT data after the correction also includes a driving magnetic field besides the resonant magnetic field generated by the LC resonance circuit 111. As shown in FIG. 4, a resonant magnetic field generated by the LC marker 10 (a vector of the resonant magnetic field expanded in a plane space indicating intensity and a phase is hereinafter referred to as F_reso) has a phase difference of 90° with respect to the driving magnetic field (a vector of the driving magnetic field expanded in a plane space indicating intensity and a phase is hereinafter referred to as F_driv). Therefore, to remove the driving magnetic field F_driv from a magnetic field included in the FFT data after the correction (this magnetic field is hereinafter referred to as "combined magnetic field" and a vector of the combined magnetic field expanded in a plane space indicating intensity and a phase is hereinafter referred to as F_dtct) and extract the resonant magnetic field F_reso, it is necessary to extract a vector component having a phase difference of 90° with respect to the driving magnetic field F_driv from the combined magnetic field F_dtct. FIG. 4 is a diagram for explaining a relation among a driving magnetic field, a combined magnetic field, and an induced magnetic field in this embodiment.

Therefore, in this embodiment, the driving coils D are driven to generate a driving magnetic field in the detection space K in a state in which the LC marker 10 (i.e., the LC resonance circuit 111) is not inserted into the detection space K. A phase component of the driving magnetic field F_driv actually detected by the sensor coils S or a not-shown magnetic field sensor arranged in the detection space K (hereinafter, "calibration information") is derived in advance. The derived calibration information is stored in the LUT or the like in association with, for example, driving information. In processing during position detection (equivalent to position detection processing explained later), the control unit 201 inputs driving information obtained when the driving-coil driving unit 220 is driven to the position-information calculating unit 214. The position-information calculating unit 214 acquires a phase of the driving magnetic field F_driv, which should be removed from the combined magnetic field F_dtct with reference to the LUT using the driving information input from the control unit 201 and extracts, based on this phase, the resonant magnetic field F_reso from the FFT data after the correction. Processing for removing the driving magnetic field F_driv from the FFT data after the correction, i.e., the combined magnetic field F_dtct is hereinafter referred to as calibration processing. Thereafter, the control unit 201 drives the position-information calculating unit 214 and executes the position calculating processing to calculate the position of the LC marker 10 from the extracted resonant magnetic field F_reso.

The position and the direction calculated through the correction processing, the calibration processing, and the position guiding processing explained above are input to the guidance-coil driving unit 230, the position and direction predicting unit 215, and the control unit 201 explained later.

The guidance-coil driving unit 230 and the guidance coils G function as a guiding unit that generates, in the detection space K, a guidance magnetic field for guiding the LC marker 10 to a position and a direction set as targets (hereinafter simply referred to as "target position and direction") and guides the LC marker 10 to the position and the direction set as the targets.

The guidance-coil driving unit 230 acquires, for example, based on the position and the direction of the LC marker 10 calculated by the position-information calculating unit 214 and the target position and direction input from the control unit 201, information for guiding the LC marker 10 to the target position and direction (hereinafter, "guidance information"), generates, based on the guidance information, one or more signal waveforms having a frequency different from the resonant frequency F0, and generates, as appropriate, a guidance signal input to one or more guidance coils G using the signal waveform. After current-amplifying the generated guidance signal as appropriate, the guidance-coil driving unit 230 outputs the guidance signal after the amplification to the guidance coil G corresponding to the guidance signal. Consequently, a guidance magnetic field for guiding the LC marker 10 to the target position and direction is generated in the detection space K. Further, the guidance-coil driving unit 230 inputs the acquired guidance information to the position and direction predicting unit 215.

For example, the operator inputs the position and the direction of the LC marker 10 set as the targets to the external apparatus 200 using the operation input unit 203. The operator can also input, for example, an instruction for acquiring intra-subject information to the LC marker 10 using the operation input unit 203.

As the guidance information, various kinds of information such as a position and a direction set as targets (target position and direction), the speed and the angular velocity of the LC marker 10 set as targets (target speed and angular velocity), and the acceleration and the angular acceleration of the LC marker 10 set as targets (target acceleration and angular acceleration) can be used. In the following explanation, three examples are explained in which the target position and direction are used, the target speed and angular velocity are used, and the target acceleration and angular acceleration are used.

The guidance information is registered in advance in a LUT or the like in association with, for example, input position and direction of the LC marker 10 and target position and direction. However, the present invention is not limited to this. The guidance information can be registered in advance in the LUT or the like in association with vector representation of a moving amount and a change amount of posture requested to the LC marker 10, which are calculated from, for example, the input position and direction of the LC marker 10 and target position and direction.

The position and direction predicting unit 215 predicts the position and the direction of the LC marker 10 at one or more kinds of timing on a time axis using the position and the direction of the LC marker 10 input from the position-information calculating unit 214 and the guidance information input from the guidance-coil driving unit 230. This processing is hereafter referred to as position and direction prediction processing. The one or more kinds of timing on the time axis are times in the past, the present, or the future with respect to the present. In other words, the position and direction predicting unit 215 can predict the position and the direction of the LC marker 10 at arbitrary timing using the input position and direction of the LC marker 10 and guidance information. In this embodiment, a period in which the position and direction predicting unit 215 predicts the position and direction of the LC marker 10 is, for example, a period in which the LC marker 10 is guided according to the guidance information. However, the present invention is not limited to this. The position and direction predicting unit 215 can also predict the position and the direction of the LC marker 10 at arbitrary timing from, for example, positions and directions and guidance information in the past according to calculation or simulation or empirically.

For example, when target position and direction are used as the guidance information, a latest position detection result (latest position and direction $(X_0, Y_0, Z_0, \theta_0, \phi_0)$) calculated by the position-information calculating unit 214 is input to the position and direction predicting unit 215 together with time when position detection is performed (hereinafter, "position detection time $T_0$"). Target position and direction (hereinafter, "target position and direction $(X, Y, Z, \theta, \phi)$") are also input to the position and direction predicting unit 215 via the control unit 201. The position and reaction predicting unit 215 calculates time when the LC marker 10 reaches the target position and direction $(X, Y, Z, \theta, \phi)$ (hereinafter, "arrival time T") from the latest position and direction $(X_0, Y_0, Z_0, \theta_0, \phi_0)$, the position detection time $T_0$, and the target position and direction $(X, Y, Z, \theta, \phi)$. The position and direction predicting unit 215 can calculate, empirically or according to simulation or the like, the arrival time T from a distance and an angle from the latest position and direction $(X_0, Y_0, Z_0, \theta_0, \phi_0)$ to the target position and direction $(X, Y, Z, \theta, \phi)$ and the position detection time $T_0$ when the latest position and direction $(X_0, Y_0, Z_0, \theta_0, \phi_0)$ are calculated.

The position and direction predicting unit 215 calculates the position and the direction of the LC marker 10 at certain time between the position detection time $T_0$ and the arrival time T (hereinafter, "prediction time $T_1$") (hereinafter, "predicted position and direction $(X_1, Y_1, Z_1, \theta_1, \phi_1)$") using the latest position and direction $(X_0, Y_0, Z_0, \theta_0, \phi_0)$, the position detection time $T_0$, and the target position and direction $(X, Y, Z, \theta, \phi)$. Specifically, the predicted position and direction $(X_1, Y_1, Z_1, \theta_1, \phi_1)$ of the LC marker 10 at the prediction time $T_1$ can be calculated using the following Equations (1) to (5). The prediction time $T_1$ is equivalent to elapsed time from the position detection time $T_0$ set as timing start time.

Latest position and direction: $(X_0, Y_0, Z_0, \theta_0, \phi_0)$
Target position and direction: $(X, Y, Z, \theta, \phi)$
Predicted position and direction: $(X_1, Y_1, Z_1, \theta_1, \phi_1)$ $$X_1 = \frac{X - X_0}{T - T_0} \times T_1 + X_0 \tag{1}$$

$$Y_1 = \frac{Y - Y_0}{T - T_0} \times T_1 + Y_0 \tag{2}$$

$$Z_1 = \frac{Z - Z_0}{T - T_0} \times T_1 + X_0 \tag{3}$$

$$\theta_1 = \frac{\theta - \theta_0}{T - T_0} \times T_1 + \theta_0 \tag{4}$$

$$\phi_1 = \frac{\phi - \phi_0}{T - T_0} \times T_1 + \phi_0 \tag{5}$$

For example, when target speed and angular velocity are used as the guidance information, besides the latest position and direction $(X_0, Y_0, Z_0, \theta_0, \phi_0)$ and the position detection time $T_0$, the speed and angular velocity of the LC marker 10 set as targets (target speed and angular velocity $(VX, VY, VZ, \omega\theta, \omega\phi)$) calculated based on the latest position and direction $(X_0, Y_0, Z_0, \theta_0, \phi_0)$ and the target position and direction $(X, Y, Z, \theta, \phi)$ by the guidance-coil driving unit 230 are input to the position and direction predicting unit 215. The position and direction predicting unit 215 calculates the predicted position and direction $(X_1, Y_1, Z_1, \theta_1, \phi_1)$ of the LC marker 10 at the prediction time $T_1$ from the latest position and direction $(X_0, Y_0, Z_0, \theta_0, \phi_0)$ and the target speed and angular velocity $(VX, VY, VZ, \omega\theta, \omega\phi)$. Specifically, the predicted position and direction $(X_1, Y_1, Z_1, \theta_1, \phi_1)$ of the LC marker 10 at the prediction time $T_1$ can be calculated using the following Equations (6) to (10). The operator can directly input the target speed and angular velocity $(VX, VY, VZ, \omega\theta, \omega\phi)$ from the operation input unit 203.

Latest position and direction: $(X_0, Y_0, Z_0, \theta_0, \phi_0)$
Target speed and angular velocity: $(VX, VY, VZ, \omega\theta, \omega\phi)$
Predicted position and direction: $(X_1, Y_1, Z_1, \theta_1, \phi_1)$ $$X_1 = \int_{T_0}^{T_1} VX \, dT + X_0 \tag{6}$$

$$Y_1 = \int_{T_0}^{T_1} VY \, dT + Y_0 \tag{7}$$

$$Z_1 = \int_{T_0}^{T_1} VZ \, dT + Z_0 \tag{8}$$

$$\theta_1 = \int_{T_0}^{T_1} \omega\theta \, dT + \theta_0 \tag{9}$$

$$\phi_1 = \int_{T_0}^{T_1} \omega\phi \, dT + \phi_0 \tag{10}$$

For example, when target acceleration and angular acceleration are used as the guidance information, besides the latest position and direction $(X_0, Y_0, Z_0, \theta_0, \phi_0)$ and the position detection time $T_0$, the acceleration and the angular acceleration of the LC marker 10 set as targets (target acceleration and angular acceleration $(AX, AY, AZ, A\theta, A\phi)$) calculated based on the latest position and direction $(X_0, Y_0, Z_0, \theta_0, \phi_0)$ and the target position and direction $(X, Y, Z, \theta, \phi)$ by the guidance-coil driving unit 230 are input to the position and direction predicting unit 215. The position and direction predicting unit 215 calculates the predicted position and direction $(X_1, Y_1, Z_1, \theta_1, \phi_1)$ of the LC marker 10 at the prediction time $T_1$ from the latest position and direction $(X_0, Y_0, Z_0, \theta_0, \phi_0)$ and the target acceleration and angular acceleration $(AX, AY, AZ, A\theta, A\phi)$. Specifically, the predicted position and direction $(X_1, Y_1, Z_1, \theta_1, \phi_0)$ of the LC marker 10 at the prediction time $T_1$ can be calculated using the following Equations (11) to (15). The operator can directly input the target acceleration and angular acceleration $(AX, AY, AZ, A\theta, A\phi)$ from the operation input unit 203. Latest position and direction: $(X_0, Y_0, Z_0, \theta_0, \phi_0)$ Target acceleration and angular acceleration: $(AX, AY, AZ, A\theta, A\phi)$ Predicted position and direction: $(X_1, Y_1, Z_1, \theta_1, \phi_1)$ $$X_1 = \int\int_{T_0}^{T_1} AX \, dT \cdot dT + X_0 \tag{11}$$

$$Y_1 = \int\int_{T_0}^{T_1} AY \, dT \cdot dT + Y_0 \tag{12}$$

$$Z_1 = \int\int_{T_0}^{T_1} AZ \, dT \cdot dT + Z_0 \tag{13}$$

$$\theta_1 = \int\int_{T_0}^{T_1} A\theta \, dT \cdot dT + \theta_0 \tag{14}$$

$$\phi_1 = \int\int_{T_0}^{T_1} A\phi \, dT \cdot dT + \phi_0 \tag{15}$$

The predicted position and direction calculated as explained above are input to the control unit 201. The control unit 201 controls to drive the driving-coil driving unit 220 based on the input predicted position and direction to generate an optimum driving magnetic field with respect to the predicted position and direction of the LC marker 10 in the detection space K. Formation of a driving magnetic field in the detection space K based on the predicted position and direction and formation of a driving magnetic field in the detection space K based on a position detection result calculated immediately before the formation (i.e., position and direction at immediately preceding timing) are explained in detail with reference to FIGS. 5 and 6. FIG. 5 is a diagram for explaining formation of a driving magnetic field in the detection space K based on a position detection result calculated immediately before the formation (i.e., a position and a direction at immediately preceding timing). FIG. 6 is a diagram for explaining formation of a driving magnetic field in the detection space K based on the predicted position and direction.

When a driving magnetic field is generated in the detection space K based on a position detection result calculated immediately before the formation, first, as shown in FIG. 5(*a*), it is assumed that, at timing t100, a position and a direction obtained by the immediately preceding position detection processing (i.e., the latest position and direction) are P0, actual position and direction of the LC marker 10 are RP1, and, in this case, both the driving coil D that generates an optimum driving magnetic field selected based on the latest position and direction P0 and the driving coil D that generates an optimum driving magnetic field that should be selected based on the actual position and direction RP1 of the LC marker 10 are driving coils D1. In this case, the optimum driving coil D with respect to the actual position and direction RP1 of the LC marker 10 and the actually selected driving coil D are the same. Therefore, a position and a direction P100 calculated by the position detection processing at this timing t100 are a position and a direction substantially the same as the actual position and direction RP1 of the LC marker 10 (P100≈RP1).

As shown in FIG. 5(b), at the next timing t200, if there is no substantial change in the moving direction and the posture change of the LC marker 10 from timing t100 to timing t200, basically, as at timing t100, both the optimum driving coil D selected based on the latest position and direction P100 and the optimum driving coil D that should be selected based on actual position and direction RP2 of the LC marker 10 are the driving coils D1. Therefore, the optimum driving coil D with respect to the actual position and direction RP2 of the LC marker 10 and the actually selected driving coil D are the same. As a result, calculated position and direction P200 are a position and a direction substantially the same as the actual position and the direction RP2 of the LC marker 10 (P200≈RP2).

However, as shown in FIG. 5(c), at the next timing t300, there is a substantial change in the moving direction and the posture change of the LC marker 10 from timing t200 to timing t300. Therefore, the optimum driving coil selected based on the latest position and direction P200 (the driving coil D1) and the optimum driving coil that should be selected based on actual position and direction RP3 of the LC marker 10 (a driving coil D2) are different. Therefore, in some case, a position and a direction P300 calculated by the position detection processing at timing t300 are substantially different from the actual position and direction RP3 of the LC marker 10 (P300≠RP3).

On the other hand, as in this embodiment, when a driving magnetic field is generated in the detection space K based on the predicted position and direction, as shown in FIG. 6(a), it is assumed that, at timing t1, a position and a direction obtained by the immediately preceding position detection processing are P0, predicted position and direction of the LC marker 10 predicted from the latest position and direction P0 are PP0, actual position and direction of the LC marker 10 are RP1, and, in this case, both the driving coil D that generates an optimum driving magnetic field selected based on the predicted position and direction PP predicted from the latest position and direction P0 according to the guidance information and the driving coil D that generates an optimum driving magnetic field that should be selected based on the actual position and direction RP1 of the LC marker 10 are the driving coils D1. In this case, the optimum driving coil D with respect to the actual position and direction RP1 of the LC marker 10 and the actually selected driving coil D are the same. Therefore, a position and a direction P1 calculated by the position detection processing at this timing t are a position and a direction substantially the same as the actual position and direction RP1 of the LC marker 10 (P1≈RP1).

As shown in FIG. 6(b), at the next timing t2, if there is no substantial change in the moving direction and the posture change of the LC marker 10 from timing t1 to timing t2, basically, as at timing t1, both the optimum driving coil D selected based on the predicted position and direction PP1 of the LC marker 10 predicted from the latest position and direction P1 according to the guidance information and the optimum driving coil D that should be selected based on actual position and direction RP2 of the LC marker 10 are the driving coils D1. Therefore, the optimum driving coil D with respect to the actual position and direction RP2 of the LC marker 10 and the actually selected driving coil D are the same. As a result, calculated position and direction P2 are a position and a direction substantially the same as the actual position and direction RP2 of the LC marker 10 (P2≈RP2).

Further, as shown in FIG. 6(c), at the next timing t3, there is a substantial change in the moving direction and the posture change of the LC marker 10 from timing t2 to timing t3. However, the position and the direction of the LC marker 10 at timing t3 are predicted using the position and direction predicting unit 215. Therefore, both the optimum driving coil D selected based on the predicted position and direction PP2 of the LC marker 10 predicted from the latest position and direction P2 according to the guidance information and the optimum driving coil D that should be selected based on actual position and direction RP3 of the LC marker 10 can be set as the driving coils D2. Consequently, the optimum driving coil D with respect to the actual position and direction RP3 of the LC marker 10 and the actually selected driving coil D are the same. As a result, calculated position and direction P3 are a position and a direction substantially the same as the actual position and direction RP3 of the LC marker 10 (P3≈RP3).

As explained above, in this embodiment, the position and the direction of the LC marker 10 are predicted at one or more kinds of timing by using the position and direction predicting unit 215 to trace the movement and the posture change of the LC marker 10 due to guidance by a guidance magnetic field. The control unit 201 selects and drives, based on the predicted position and direction, the driving coil D that generates an optimum driving magnetic field in the detection space K. Therefore, it is possible to stably generate a satisfactory resonant magnetic field in the LC marker 10. As a result, it is possible to improve position detection accuracy of the position detecting system 1.

Operation

The position detection processing executed by the position detecting system 1 according to this embodiment is explained in detail below with reference to the accompanying drawings. FIG. 7 is a flowchart for explaining an overview of the position detection processing according to this embodiment. In the following explanation, attention is paid to the operation of the control unit 201 that controls to drive the units in the external apparatus 200.

As shown in FIG. 7, in the position detection processing according to this embodiment, first, the control unit 201 drives the driving-coil driving unit 220 based on initial setting to generate a driving magnetic field in the detection space K (step S101: driving-magnetic-field generating step). In generating the driving magnetic field, the control unit 201 performs, in this recited order, a driving-signal generating step for generating, with the driving-signal generating unit 221, a driving signal having a specific frequency that should be input to the driving coil D, a driving-coil selecting step for selecting, with the driving-coil switching unit 222, out of the driving coils D, the driving coil D to which the driving signal generated at the driving-signal generating step is input, and a driving-signal input step for inputting the driving signal to the driving coil D. A resonant magnetic field is generated from the LC marker 10 according to the formation of the driving magnetic field (a resonant-magnetic-field generating step).

Subsequently, the control unit 201 drives the sense-coil selecting unit 212 and selects the sense coils S_1, S_2, and the like to cause the signal detecting unit 211 to read out detection signals of the selected sense coils S (a magnetic-field detecting step) and inputs FFT data generated by the signal detecting unit 211 from the detection signals, which are read out from the sense coils S, to the interference correcting unit 213 (step S102). The signal detecting unit 211 reads out the detection signals from the sense coils S, for example, periodically and executes predetermined signal processing on the detection signals to generate the FFT data. The sense coils S that the control unit 201 causes the sense-coil selecting unit 212 to select at step S102 do not need to be all the sense coils S and can be a part of the sense coils S.

The control unit 201 drives the interference correcting unit 213 to correct the FFT data output from the signal detecting unit 211 (step S103: correction processing). Specifically, the control unit 201 refers to the memory unit 202 using a position and a direction input from the position-information calculating unit 214 immediately before the correction (i.e., the last position and direction) to acquire a correction amount corresponding to the position and the direction and corrects the FFT data using the correction amount. Consequently, an interference magnetic field included in the FFT data is removed. The FFT data after the correction is input to the position-information calculating unit 214.

The control unit 201 drives the position-information calculating unit 214 to calculate the position and the direction of the LC marker 10 from the FFT data after the correction (step S104 (a position detecting step): calibration processing and position calculating processing). Specifically, the control unit 201 removes a component of the driving magnetic field included in the FFT data to extract a component of the resonant magnetic field according to the calibration processing. Subsequently, the control unit 201 calculates the position and the direction of the LC marker 10 using the extracted component of the resonant magnetic field according to the position calculating processing. The calculated position and direction are input to the guidance-coil driving unit 230 and the position and direction predicting unit 215. The guidance-coil driving unit 230 according to this embodiment generates a guidance magnetic field in the detection space K based on the latest position and direction input from the position-information calculating unit 214 and the target position and direction input from the control unit 201 to guide the LC marker 10 to the target position and direction.

The control unit 201 drives the position and direction predicting unit 215 to predict the position and the direction of the LC marker 10, for example, at timing when step S102 is executed next (step S105 (a predicting step): position and direction prediction processing). Guidance information is input to the position and direction predicting unit 215 from the guidance-coil driving unit 230 as appropriate or periodically. Therefore, the position and direction predicting unit 215 predicts, based on the latest position and direction input from the position-information calculating unit 214 as a result of step S104 and the guidance information input from the guidance-coil driving unit 230 as appropriate or periodically, the position and the direction of the LC marker 10 at timing when step S102 is executed next. The predicted position and direction are input to the control unit 201.

The control unit 201 drives the driving-coil driving unit 220 based on the predicted position and direction input at step S105 to generate, in the detection space K, a driving magnetic field that is optimum when the LC marker 10 is in the predicted position and direction (step S106: a control step). Specifically, the control unit 201 refers to the memory unit 202 using the input predicted position and direction to acquire driving information associated with the predicted position and direction. Subsequently, the control unit 201 drives the driving-coil switching unit 222 according to the acquired driving information to select the driving coil D that can generate an optimum driving magnetic field with respect to the LC marker 10 present in the predicted position and direction. The control unit 201 inputs the driving signal, which is output from the driving-signal generating unit 221, to the driving coil D. Consequently, a driving magnetic field that is optimum when the LC marker 10 is in the predicted position and direction is generated in the detection space K.

Thereafter, the control unit 201 determines whether an end instruction is input from the operator, for example, via the operation input unit 203 (step S107). When the end instruction is not input (No at step S107), the control unit 201 returns to step S102 and thereafter executes operation same as that explained above. On the other hand, when the end instruction is input (Yes at step S107), the control unit 201 ends the processing.

With the configuration and the operation explained above, in this embodiment, it is possible to generate a resonant magnetic field having high intensity in the LC marker 10 present in actual position and direction. As a result, it is possible to improve accuracy of a position detection result. For example, the direction of the driving magnetic field generated in the detection space K and a space distribution of intensity of the driving magnetic field change depending on the driving coils D in use. Therefore, in this embodiment, the driving coil D is selected such that a driving magnetic field having high intensity and generated in a suitable direction is generated in the predicted position and direction. This makes it possible to input the driving magnetic field having high intensity and generated in the suitable direction to the LC marker 10 present in the actual position and direction close to the predicted position and direction. As a result, it is possible to generate a resonant magnetic field having high intensity and accurately perform position detection.

In a method of using the appropriate driving coil D for the LC marker 10 present in a position and a direction calculated immediately before the use, in some case, the driving coil D in use is not always the appropriate driving coil D for the LC marker 10 in the next position detection. On the other hand, in this embodiment, the movement and the posture change of the LC marker 10 in future are predicted and the driving coil D in use is selected according to predicted position and direction. Therefore, it is possible to always select the appropriate driving coil D. As a result, it is possible to stably execute highly accurate position detection.

First Modification

In this embodiment, besides the driving coil D in use, a driving signal input to the driving coil D can also be changed according to predicted position and direction. An example of this case is explained as a first modification.

In the first modification, the position and direction predicting unit 215 controls to drive both the driving-coil switching unit 222 and the driving-signal generating unit 221 based on predicted position and direction calculated by the position and direction predicting unit 215. In other words, the control unit 201 switches, based on the predicted position and direction, information for controlling to drive the driving-coil switching unit 222 and the driving-signal generating unit 221 (equivalent to driving information explained later) and controls to drive the driving-coil switching unit 222 and the driving-signal generating unit 221 according to the driving information.

Specifically, at step S105 shown in FIG. 7, the control unit 201 refers to the memory unit 202 using the input predicted position and direction to acquire driving information associated with the predicted position and direction. Subsequently, the control unit 201 drives the driving-coil switching unit 222 according to the acquired driving information to select the driving coil D that can generate an optimum driving magnetic field for the LC marker 10 present in the predicted position and direction. The control unit 201 also drives the driving-signal generating unit 221 according to the acquired driving information to generate a driving signal for generating an optimum driving magnetic field and inputs the driving signal to the selected driving coil D using the driving-coil switching unit 222. Consequently, a driving magnetic field that is optimum when the LC marker 10 is present in the predicted position and direction is generated in the detection space K.

With the configuration and the operation explained above, in the first modification, the driving signal for generating an optimum driving magnetic field is input to the driving coil D that can generate a driving magnetic field that is optimum when the LC marker 10 is in the predicted position and direction. Therefore, it is possible to stably execute more highly accurate position detection. In other words, it is possible to accurately generate a driving magnetic field having high intensity and generated in a suitable direction according to predicted position and direction. Therefore, it is possible to input the driving magnetic field having high intensity and generated in the suitable direction to the LC marker 10 present in actual position and direction close to the predicted position and direction. As a result, it is possible to generate a resonant magnetic field having higher intensity and more accurately perform position detection.

Second Modification

In this embodiment, as explained above, all the sense coils S selected by the sense-coil selecting unit 212 do not need to be all the sense coils S and can be a part of the sense coils S. An example of this case is explained as a second modification below.

A distribution of resonant magnetic fields detected by the sense coils S changes according to the position and the direction of the LC marker 10 that is a generation source of the resonant magnetic fields. Therefore, the sense coils S effective for accurate position detection change depending on the position and the direction of the LC marker 10. In other words, the sense coils S to which a resonant magnetic field having high intensity is input and the sense coils S that can detect a resonant magnetic field without saturating change depending on the position and the direction of the LC marker 10.

Therefore, in the second modification, the control unit 201 selects one or more sense coils S as readout targets according to predicted position and direction input from the position and direction predicting unit 215 and drives the sense-coil selecting unit 212 based on the selection. This makes it possible to set, as processing targets of the interference correcting unit 213 and the units following the interference correcting unit 213, only FFT data generated by detection signals read out from one or more sense coils S effective for accurate position detection. Therefore, it is possible to efficiently execute accurate position detection.

Information concerning association of a position and a direction and the sense coils S as readout targets can be acquired in advance, for example, by simulation or actual measurement. The acquired association information is managed, for example, by the memory unit 202. In an operation during readout (see, for example, step S102 in FIG. 7), the control unit 201 acquires identification information of the sense coils S as readout targets from the memory unit 202 using predicted position and direction and drives the sense-coil selecting unit 212 according to the identification information to input, to the interference correcting unit 213, only the FFT data generated by the detection signals read out from the one or more sense coils S effective for accurate position detection.

Third Modification

To calculate a position and a direction using the correction processing, the calibration processing, and the position calculating processing, for example, it is possible to apply a convergence calculation employing the method of least squares. An example of this case is explained as a third modification.

In the convergence calculation in the third modification, the position-information calculating unit 214 sets, as a true value, a magnetic field distribution of a resonant magnetic field included in a detection signal read out from a sense coil (i.e., a magnetic field distribution of a resonant magnetic field indicated by FFT data after the calibration processing) and sets, as an initial value of an estimation value, a magnetic field distribution of a resonant magnetic field generated by the LC marker 10 (or a magnetic moment equivalent to the LC marker 10) when it is assumed that the LC marker 10 (or the magnetic moment equivalent to the LC marker 10) is present in predicted position and direction predicted by the position and direction predicting unit 215.

In the convergence calculation by the method of least squares explained above, it is possible to cause a value to converge with smaller iteration as the initial value of the estimation value is closer to the true value. As a result, it is possible to reduce processing time and reduce a processing amount.

Therefore, in the third modification, a magnetic field distribution of resonant magnetic field that can be back-calculated from predicted position and direction close to the actual position and direction of the LC marker 10 is used as the initial value of the estimation value. This makes it possible to set the estimation value (the magnetic field distribution back-calculated from the predicted position and reaction) and the true value (the magnetic field distribution of the resonant magnetic fields indicated by the FFT data after the calibration processing) to close values. Therefore, it is possible to quickly and more accurately calculate the position and the direction of the LC marker 10.

Fourth Modification

In this embodiment, it is also possible that the interference correcting unit 213 corrects FFT data using a correction amount corresponding to predicted position and direction calculated by the position and direction predicting unit 215. An example of this case is explained as a fourth modification below.

In correction processing during position detection in the fourth modification (see step S103 in FIG. 7), the control unit 201 refers to the LUT in the memory unit 202 using predicted position and direction calculated by the position and direction predicting unit 215 to acquire a correction amount associated with the predicted position and direction and inputs the correction amount to the interference correcting unit 213. The interference correcting unit 213 executes the correction processing using FFT data input via the sense-coil selecting unit 212 and the correction amount input from the control unit 201 to remove a component of an interference magnetic field from the FFT data according to the predicted position and direction.

With the configuration and the operation explained above, in the fourth modification, the FFT data is corrected by using the correction amount corresponding to the predicted position and direction close to the actual position and direction of the LC marker 10. Therefore, it is possible to improve accuracy of a position detection result by the position detection processing.

As in the third modification, when position detection is performed by using the convergence calculation, the FFT data after the correction set as the true value is a more accurate value. Therefore, it is possible to further reduce a difference between the true value and the estimation value. This makes it possible to reduce the number of times of iteration until convergence. Therefore, it is possible to more quickly calculate more accurate position and direction.

Fifth Modification

Depending on a moving passage of the LC marker 10, switching of the driving coils D by the driving-coil switching unit 222 frequently occurs. Therefore, an example of a form in which frequent occurrence of switching of the driving coils D can be suppressed is explained as a fifth modification below.

In this embodiment, as explained above, the position and direction predicting unit 215 can predict the position and the direction of the LC marker 10 at one or more kinds of timing on the time axis. Therefore, in the fifth modification, the position and direction predicting unit 215 predicts positions and directions at a plurality of kinds of timing in future. The control unit 201 determines, according to a plurality of predicted positions and directions, whether frequent switching of the driving coils D occurs. This determination is executed, for example, at step S107 in FIG. 7. This determination can be performed based on, for example, whether the driving coils D determined as optimum at the respective kinds of timing are alternately switched on a time sequence. The alternate switching on the time sequence indicates that, for example, switching such as the driving coil D1→the driving coil D2→the driving coil D1 or switching such as the driving coil D1→the driving coil D2→the driving coil D3 occurs along timing arrayed on the time axis.

As a result of the determination, when it is determined that the frequent switching of the driving coils D occurs, the control unit 201 specifies, for example, the driving coil D predicted as being most frequently used in a predicted range. When the driving coil D different from this driving coil D is determined as optimum, the control unit 201 selects the driving coil D determined as optimum in a position and a direction at immediately following timing. For example, when the switching such as the driving coil D1→the driving coil D2→the driving coil D1 or the switching such as the driving coil D1→the driving coil D2→the driving coil D3 occurs as in the example explained above, the control unit 201 switches the driving coils in such a manner as the driving coil D1→the driving coil D2→the driving coil D1 or the driving coil D1→the driving coil D2→the driving coil D3.

With the operation explained above, in the fifth modification, it is possible to suppress frequent switching of the driving coils D. As a result, it is possible to smoothly and accurately execute position detection and magnetic guidance.

Second Embodiment

The configuration and the operation of a position detecting system 2 according to a second embodiment of the present invention are explained in detail below with reference to the accompanying drawings. In the following explanation, components same as those in the first embodiment are denoted by the same reference numerals and signs and detailed explanation of the components is omitted.

FIG. 8 is a schematic diagram of a schematic configuration of the position detecting system 2 according to this embodiment. As it is evident when FIG. 8 and FIG. 1 are compared, in the position detecting system 2, in the configuration same as that of the position detecting system 1 according to the first embodiment, the position and direction predicting unit 215 is replaced with a position and direction predicting unit 215A. In FIG. 8, the guidance driving unit 230 and the guidance coil G, i.e., the configuration (the guiding unit) for guiding the LC marker 10 is omitted. However, the present invention is not limited to this.

In this embodiment, a position and a direction calculated by the position-information calculating unit 214 are input to the position and direction predicting unit 215A and input to the memory unit 202 and stored therein. The position and direction predicting unit 215A can refer to the memory unit 202 as appropriate.

When latest position and direction is input to the position and direction predicting unit 215A from the position-information calculating unit 214, the position and direction predicting unit 215A acquires a position and a direction acquired last time referring to the memory unit 202. The position and direction predicting unit 215A calculates the speed and the angular velocity of the LC marker 10 based on, for example, the following Equations (16) to (20) from the acquired latest position and direction and the position and the direction acquired last time. In Equations (16) to (20), the latest position and direction are represented as "position and direction at time $T_{11}$", the position and the direction acquired last time are represented as "position and direction at time $T_{10}$", and the speed and the angular velocity of the LC marker 10 at a point of time $T_{11}$ is represented as "speed and angular velocity at time $T_{11}$".

Position and direction at time $T_{11}$: $(X_{11}, Y_{11}, Z_{11}, \theta_{11}, \phi_{11})$
Position and direction at time $T_{10}$: $(X_{10}, Y_{10}, Z_{10}, \theta_{10}, \phi_{10})$
Speed and angular velocity at time $T_{11}$: $(VX_{11}, VY_{11}, VZ_{11}, \omega\theta_{11}, \omega\phi_{11})$ $$VX_{11} = \frac{X_{11} - X_{10}}{T_{11} - T_{10}} \quad (16)$$

$$VY_{11} = \frac{Y_{11} - Y_{10}}{T_{11} - T_{10}} \quad (17)$$

$$VZ_{11} = \frac{Z_{11} - Z_{10}}{T_{11} - T_{10}} \quad (18)$$

$$\omega\theta_{11} = \frac{\theta_{11} - \theta_{10}}{T_{11} - T_{10}} \quad (19)$$

$$\omega\phi_{11} = \frac{\phi_{11} - \phi_{10}}{T_{11} - T_{10}} \quad (20)$$

When the speed and the angular velocity of the LC marker 10 at time $T_{11}$ is calculated as explained above, subsequently, the position and direction predicting unit 215A calculates the position and the direction of the LC marker 10 at arbitrary timing (time $T_{12}$) using the following Equations (21) to (25) in the same manner as calculating position and direction when the guidance information is speed and angular velocity in the first embodiment (see Equations (6) to (10)). In Equations (21) to (25), the position and the direction of the LC marker 10 at arbitrary time $T_{12}$ is represented as "predicted position and direction at time $T_{12}$".

Predicted position and direction at time $T_{12}$: $(X_{12}, Y_{12}, Z_{12}, \theta_{12}, \phi_{12})$ $$X_{12} = VX_{11} \times (T_{12} - T_{11}) + X_{11} \quad (21)$$

$$Y_{12} = VY_{11} \times (T_{12} - T_{11}) + Y_{11} \quad (22)$$

$$Z_{12} = VZ_{11} \times (T_{12} - T_{11}) + Z_{11} \quad (23)$$

$$\theta_{12} = \omega\theta_{11} \times (T_{12} - T_{11}) + \theta_{11} \quad (24)$$

$$\phi_{12} = \omega\phi_{11} \times (T_{12} - T_{11}) + \phi_{11} \quad (25)$$

As explained above, in this embodiment, it is possible to predict a position and a direction at arbitrary timing of the LC marker 10 without using the guidance information. As a result, in this embodiment, as in the first embodiment, it is possible to cause the LC marker 10 present in the actual position and direction to generate a resonant magnetic field having stable and high intensity. As a result, it is possible to improve accuracy of a position detection result. In this embodiment, as in the first embodiment, the movement and the posture change of the LC marker 10 in future are predicted and the driving coil D in use is selected according to predicted position and direction. Therefore, it is possible to always select the appropriate driving coil D. As a result, it is possible to stably execute highly accurate position detection.

The other components and operations are the same as those in the first embodiment or the modifications thereof. Therefore, detailed explanation of the components and operations is omitted.

In the examples explained in the first and second embodiments, the LC marker 10 is guided to both of a position and a direction. However, the present invention is not limited to this. The LC marker 10 may be guided with only one of the position and the direction set as a target. The embodiments are merely examples for carrying out the present invention. The present invention is not limited to the embodiments. It is obvious from the above description that it is within the scope of the present invention to variously modify the embodiments according to specifications and the like and other various embodiments are possible within the scope of the present invention.

In a position detecting method according to the embodiments, the coils arranged near the detection space are driving coils that generate driving magnetic field.

In the position detecting method according to the embodiments, the position detecting system includes a guiding unit that guides at least one of a position and a direction of the body-insertable apparatus to at least one of a position and a direction set as targets. The body-insertable apparatus includes a magnet fixed to a housing of the body-insertable apparatus. The guiding unit includes guidance coils that generate guidance magnetic fields acting on the magnet. The coils arranged near the detection space are the guidance coils.

What is claimed is:

1. A position detecting system comprising:
a detected object including a magnetic-field generating unit that generates a magnetic field;
at least one magnetic sensor configured to detect the magnetic field generated by the magnetic-field generating unit;
a position detecting unit configured to calculate, based on a detection value of the at least one magnetic sensor, at least one of a position and a direction of the detected object;
a memory unit configured to store a calculation result of the position detecting unit;
a predicting unit configured to calculate, based on the calculation results at a plurality of times different from one another stored in the memory unit, a moving amount by which the detected object is predicted to move between a first time when the position detecting unit calculates the at least one of the position and the direction of the detected object and a second time after a predetermined time from the first time, and to predict, based on a calculation result of the position detecting unit at the first time stored in the memory unit and the moving-amount calculation result, at least one of a position and a direction of the detected object at the second time; and
a control unit configured to control the position detecting unit based on the at least one of the position and the direction of the detected object at the second time predicted by the predicting unit, wherein:
the position detecting unit is configured to change, when a detection value of the at least one magnetic sensor is set as a true value and a predicted value of the magnetic sensor predicted under an assumption that the detected object is present in an estimation position is set as an estimation value, the estimation position such that a difference between the true value and the estimation value is equal to or smaller than a predetermined value, and
the control unit is configured to change an initial value of the estimation position.

2. The position detecting system according to claim 1, wherein
the position detecting unit includes a magnetic-sensor selecting unit that selects at least one of the magnetic sensors that is a target from which the detection value is read out, and
the control unit is configured to control the magnetic-sensor selecting unit to select the at least one of the magnetic sensors.

3. The position detecting system according to claim 1, wherein
the magnetic-field generating unit includes a resonance circuit that is induced by a driving magnetic field having a specific frequency to generate the magnetic field as a resonant magnetic field,
the position detecting system further comprises a driving-magnetic-field generating unit that generates the driving magnetic field having the specific frequency, and
the control unit is further configured to control the driving-magnetic-field generating unit.

4. The position detecting system according to claim 3, wherein
the driving-magnetic-field generating unit includes
a driving coil that generates the driving magnetic field; and
a driving-signal generating unit that generates a driving signal having a frequency same as the specific frequency and inputs the driving signal to the driving coil, and
the control unit is further configured to control generation of the driving signal by the driving-signal generating unit.

5. The position detecting system according to claim 3, wherein the driving-magnetic-field generating unit includes
a plurality of driving coils that generate the driving magnetic field;
a driving-signal generating unit that generates a driving signal having the specific frequency; and
a switching unit that switches, among the driving coils, a driving coil to which the driving signal generated by the driving-signal generating unit should be input, and
the control unit is further configured to control switching of the driving coil by the switching unit.

6. A position detecting system comprising:
a detected object that includes a magnetic-field generating unit that generates a magnetic field;
at least one magnetic sensor that detects the magnetic field generated by the magnetic-field generating unit;
a position detecting unit that calculates, based on a detection value of the at least one magnetic sensor, at least one of a position and a direction of the detected object;
a memory unit that stores a calculation result of the position detecting unit;
a moving-amount calculating unit that calculates, based on the calculation results at a plurality of times different from one another stored in the memory unit, a moving amount by which the detected object is predicted to move between first time when the position detecting unit calculates the at least one of the position and the direction of the detected object and second time after a predetermined time from the first time;

a predicting unit that predicts, based on a calculation result of the position detecting unit at the first time stored in the memory unit and a calculation result of the moving-amount calculating unit, at least one of a position and a direction of the detected object at the second time; and a control unit that controls the position detecting unit based on the at least one of the position and the direction of the detected object at the second time predicted by the predicting unit, wherein the position detecting unit includes an interference correcting unit that corrects the detection value by removing, from the detection value, a component of an interference magnetic field, which is caused when a coil arranged near the magnetic-field generating unit is induced by the magnetic field, in the detection value, and the control unit is further configured to change the component of the interference magnetic field that should be removed by the interference correcting unit.

7. The position detecting system according to claim 6, wherein the magnetic-field generating unit includes a resonance circuit that generates a resonant magnetic field induced by a driving magnetic field having a specific frequency, the position detecting system further comprises a driving-magnetic-field generating unit that generates the driving magnetic field, and the control unit is configured to control the driving-magnetic-field generating unit.

8. The position detecting system according to claim 7, wherein the driving-magnetic-field generating unit includes
   a driving coil that generates the driving magnetic field; and
   a driving-signal generating unit that generates a driving signal having a frequency same as the specific frequency and inputs the driving signal to the driving coil, and the control unit is configured to control generation of the driving signal by the driving-signal generating unit.

9. The position detecting system according to claim 7, wherein the driving-magnetic-field generating unit includes
   a plurality of driving coils that generate the driving magnetic field;
   a driving-signal generating unit that generates a driving signal having the specific frequency; and
   a switching unit that switches, among the driving coils, a driving coil to which the driving signal generated by the driving-signal generating unit should be input, and the control unit is configured to control switching of the driving coil by the switching unit.

10. A method for operating a position detecting system, the position detecting system including a detected object that includes a magnetic-field generating unit that generates a magnetic field; at least one magnetic sensor that detects the magnetic field generated by the magnetic-field generating unit; a position detecting unit that calculates, based on a detection value of the at least one magnetic sensor, at least one of a position and a direction of the detected object; a moving-amount calculating unit that calculates a moving amount of the detected object; a predicting unit that predicts, based on a calculation result of the position detecting unit and a calculation result of the moving-amount calculating unit, at least one of a position and a direction of the detected object; and a control unit that controls the position detecting unit based on the at least one of the position and the direction of the detected object predicted by the predicting unit, the method comprising:

detecting, with the at least one magnetic sensor, a magnetic field generated by the magnetic-field generating unit;

performing, by the position detecting unit, when a detection value of the magnetic sensor that detects the magnetic field is set as a true value and a predicted value of the magnetic sensor predicted under an assumption that the detected object is present in an estimation position is set as an estimation value, convergence calculation for changing the estimation position such that a difference between the true value and the estimation value is equal to or smaller than a predetermined value to calculate at least one of a position and a direction of the detected object;

calculating, by the moving-amount calculating unit, a moving amount by which the detected object is predicted to move between first time when the at least one of the position and the direction of the detected object is calculated and second time after a predetermined time from the first time;

predicting, by the predicting unit, based on a result of the calculation performed at the first time and a result of the calculation of the moving amount, at least one of a position and a direction of the detected object at the second time; and chancing, by the control unit, an initial value of the estimation position based on the predicted at least one of the position and the direction of the detected object at the second time.

11. A method for operating a position detecting system, the position detecting system including a detected object that includes a magnetic-field generating unit that generates a magnetic field; at least one magnetic sensor that detects the magnetic field generated by the magnetic-field generating unit; a position detecting unit that calculates, based on a detection value of the at least one magnetic sensor, at least one of a position and a direction of the detected object; a moving-amount calculating unit that calculates a moving amount of the detected object; a predicting unit that predicts, based on a calculation result of the position detecting unit and a calculation result of the moving-amount calculating unit, at least one of a position and a direction of the detected object; and a control unit that controls the position detecting unit based on the at least one of the position and the direction of the detected object predicted by the predicting unit, the method comprising:

detecting, with the at least one magnetic sensor, a magnetic field generated by the magnetic-field generating unit;

correcting, by the position detecting unit, the detection value by removing, from a detection value of the magnetic sensor that detects the magnetic field, a component of an interference magnetic field, which is caused when a coil arranged near the magnetic-field generating unit is induced by the magnetic field, in the detection value and calculating, based on the detection value after the correction, at least one of a position and a direction of the detected object;

calculating, by the moving-amount calculating unit, a moving amount by which the detected object is predicted to move between first time when the at least one of the position and the direction of the detected object is calculated and second time after a predetermined time from the first time;

predicting, by the predicting unit, based on a result of the calculation performed at the first time and a result of the calculation of the moving amount, at least one of a position and a direction of the detected object at the second time; and changing, by the control unit, based on the predicted at least one of the position and the direction of the detected object at the second time, the component of the interference magnetic field that should be removed from the detection value of the magnetic sensor.

12. A method for operating a position detecting system, the position detecting system including a detected object that includes a magnet and a magnetic-field generating unit that generates a magnetic field; at least one magnetic sensor that detects the magnetic field generated by the magnetic-field generating unit; a position detecting unit that calculates, based on a detection value of the at least one magnetic sensor, at least one of a position and a direction of the detected object; a guidance-magnetic-field generating unit that generates a guidance magnetic field acting on the magnet; a guiding unit that guides the at least one of the position and the direction of the detected object to at least one of a position and a direction set as targets; a moving-amount calculating unit that calculates a moving amount of the detected object; a predicting unit that predicts, based on a calculation result of the position detecting unit and a calculation result of the moving-amount calculating unit, at least one of a position and a direction of the detected object; and a position detection control unit that controls the position detecting unit based on the at least one of the position and the direction of the detected object predicted by the predicting unit, the method comprising:

detecting, with the at least one magnetic sensor, a magnetic field generated by the magnetic-field generating unit;
  performing, by the position detecting unit, when a detection value of the magnetic sensor that detects the magnetic field is set as a true value and a predicted value of the magnetic sensor predicted under an assumption that the detected object is present in an estimation position is set as an estimation value, convergence calculation for changing the estimation position such that a difference between the true value and the estimation value is equal to or smaller than a predetermined value to calculate at least one of a position and a direction of the detected object;
  generating, by the guidance-magnetic-field generating unit, based on guide information as information concerning any one of a position and a direction set as targets or both concerning the detected object, information concerning any one of target speed of the detected object and target angular velocity of the detected object or both, or information concerning any one of target acceleration of the detected object and target angular acceleration of the detected object or both, a guidance magnetic field acting on the magnet;
  controlling, by the guiding unit, the guidance-magnetic-field generating unit to guide the detected object from the at least one of a position and a direction of the detected object calculated by the position detecting unit to at least one of a position and a direction set as targets;
  calculating, by the moving-amount calculating unit, a moving amount by which the detected object is predicted to move between first time when the at least one of the position and the direction of the detected object is calculated and second time after a predetermined time from the first time;
  predicting, by the predicting unit, based on a result of the calculation performed at the first time and a result of the calculation of the moving amount, at least one of a position and a direction of the detected object at the second time; and
  changing, by the position detection control unit, an initial value of the estimation position based on the predicted at least one of the position and the direction of the detected object at the second time.

13. A method for operating a position detecting system, the position detecting system including a detected object that includes a magnet and a magnetic-field generating unit that generates a magnetic field; at least one magnetic sensor that detects the magnetic field generated by the magnetic-field generating unit; a position detecting unit that calculates, based on a detection value of the at least one magnetic sensor, at least one of a position and a direction of the detected object; a guidance-magnetic-field generating unit that generates a guidance magnetic field acting on the magnet; a guiding unit that guides the at least one of the position and the direction of the detected object to at least one of a position and a direction set as targets; a moving-amount calculating unit that calculates a moving amount of the detected object; a predicting unit that predicts, based on a calculation result of the position detecting unit and a calculation result of the moving-amount calculating unit, at least one of a position and a direction of the detected object; and a control unit that controls the position detecting unit based on the at least one of the position and the direction of the detected object predicted by the predicting unit, the method comprising:

detecting, with the at least one magnetic sensor, a magnetic field generated by the magnetic-field generating unit;
  correcting, by the position detecting unit, the detection value by removing, from a detection value of the magnetic sensor that detects the magnetic field, a component of an interference magnetic field, which is caused when a coil arranged near the magnetic-field generating unit is induced by the magnetic field, in the detection value to calculate, based on the detection value after the correction, at least one of a position and a direction of the detected object;
  generating, by the guidance-magnetic-field generating unit, based on guide information as information concerning any one of a position and a direction set as targets or both concerning the detected object, information concerning any one of target speed of the detected object and target angular velocity of the detected object or both, or information concerning any one of target acceleration of the detected object and target angular acceleration of the detected object or both, a guidance magnetic field acting on the magnet;
  controlling, by the guiding unit, the guidance-magnetic-field generating unit to guide the detected object from the at least one of a position and a direction of the detected object to at least one of a position and a direction set as targets;
  calculating, by the moving-amount calculating unit, a moving amount by which the detected object is predicted to move between first time when the at least one of the position and the direction of the detected object is calculated and second time after a predetermined time from the first time;
  predicting, by the predicting unit, based on a result of the calculation performed at the first time and a result of the calculation of the moving amount, at least one of a position and a direction of the detected object at the second time; and changing, by the control unit, based on the predicted at least one of the position and the direction of the detected object at the second time, the component of the interference magnetic field that should be removed from the detection value of the magnetic sensor.

14. A position detecting system comprising:
a body-insertable apparatus that generates a resonant magnetic field induced by a driving magnetic field having a specific frequency;
a driving-magnetic-field generating unit that generates the driving magnetic field having the specific frequency in a detection space surrounding a subject into which the body-insertable apparatus is inserted;
a magnetic sensor that detects a magnetic field generated in the detection space;
a position detecting unit that detects, based on the magnetic field detected by the magnetic sensor, at least one of a position and a direction of the body-insertable apparatus;
a predicting unit that predicts, based on the at least one of the position and the direction at different times detected by the position detecting unit, at least one of a position and a direction at a certain time of the body-insertable apparatus; and
a control unit that controls the driving-magnetic-field generating unit and the position detecting unit based on the at least one of the position and the direction at the certain time predicted by the predicting unit,
wherein the position detecting unit is configured to:
set, as a true value, a magnetic field distribution of the resonant magnetic field included in the magnetic field detected by the magnetic sensor,
set, as an initial value of an estimation value, a magnetic field distribution of a resonant magnetic field generated by the body-insertable apparatus under an assumption that the body-insertable apparatus is in the at least one of the position and the direction at the certain time predicted by the predicting unit, and
detect the at least one of the position and the direction by a convergence calculation employing a method of least squares.

15. The position detecting system according to claim 14, further comprising:
a plurality of the magnetic sensor; and
a selecting unit that selects at least one magnetic sensor that is to read out the magnetic field from the plurality of the magnetic sensor,
wherein the control unit is configured to control the selecting unit based on the at least one of the position and the direction at the certain time predicted by the predicting unit.

16. A position detecting system, comprising:
a body-insertable apparatus that generates a resonant magnetic field induced by a driving magnetic field having a specific frequency;
a driving-magnetic-field generating unit that generates the driving magnetic field having the specific frequency in a detection space in which a subject into which the body-insertable apparatus is inserted is placed;
a magnetic sensor that detects a magnetic field generated in the detection space;
a position detecting unit that detects at least one of a position and a direction of the body-insertable apparatus based on the magnetic field detected by the magnetic sensor;
a predicting unit that predicts at least one of a position and a direction of the body-insertable apparatus at a certain time based on at least one of the positions and the directions at different times detected by the position detecting unit; and
a control unit that controls the driving-magnetic-field generating unit and the position detecting unit based on the at least one of the position and the direction at the certain time predicted by the predicting unit, wherein
the position detecting unit includes an interference correcting unit that corrects the magnetic field by removing from the magnetic field a component of interference magnetic field caused when a coil arranged near the detection space is induced by the resonant magnetic field, and
the interference correcting unit removes from the magnetic field a magnetic field component other than the resonant magnetic field included in the magnetic field based on the at least one of the position and the direction at the certain time predicted by the predicting unit.

17. The position detecting system according to claim 16, wherein
the body-insertable apparatus includes a magnet that is fixed to a housing of the body-insertable apparatus,
a guiding unit includes a guidance coil for generating a guidance magnetic field acting on the magnet, and
the coil arranged near the detection space is the guidance coil.

18. The position detecting system according to claim 16, further comprising:
a plurality of the magnetic sensor; and
a selecting unit that selects at least one magnetic sensor that is to read out the magnetic field from the plurality of the magnetic sensor,
wherein the control unit is configured to control the selecting unit based on the at least one of the position and the direction at the certain time predicted by the predicting unit.

* * * * *